US012570720B2

(12) United States Patent
Procko

(10) Patent No.: US 12,570,720 B2
(45) Date of Patent: Mar. 10, 2026

(54) ENGINEERED RECEPTORS FOR HUMAN CYTOMEGALOVIRUS AND USES THEREOF

(71) Applicant: The Board of Trustees of the University of Illinois, Urbana, IL (US)

(72) Inventor: Erik Procko, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 997 days.

(21) Appl. No.: 17/761,051

(22) PCT Filed: Sep. 15, 2020

(86) PCT No.: PCT/US2020/050903
§ 371 (c)(1),
(2) Date: Mar. 16, 2022

(87) PCT Pub. No.: WO2021/055367
PCT Pub. Date: Mar. 25, 2021

(65) Prior Publication Data
US 2022/0380436 A1 Dec. 1, 2022

Related U.S. Application Data

(60) Provisional application No. 62/901,397, filed on Sep. 17, 2019.

(51) Int. Cl.
*C07K 14/71* (2006.01)
*A61P 31/20* (2006.01)
(52) U.S. Cl.
CPC .............. *C07K 14/71* (2013.01); *A61P 31/20* (2018.01); *C07K 2319/30* (2013.01)
(58) Field of Classification Search
None
See application file for complete search history.

(56) References Cited

U.S. PATENT DOCUMENTS

| | | | | | |
|---|---|---|---|---|---|
| 5,686,572 | A | * | 11/1997 | Wolf | C07K 14/71 |
| | | | | | 530/402 |
| 6,667,173 | B2 | | 12/2003 | Kazlauskas et al. | |
| 2009/0203541 | A1 | | 8/2009 | West | |
| 2010/0210829 | A1 | | 8/2010 | Linnemann et al. | |
| 2011/0311523 | A1 | | 12/2011 | Cobbs et al. | |
| 2019/0161532 | A1 | | 5/2019 | Sinzger et al. | |

FOREIGN PATENT DOCUMENTS

WO        WO 03/105773        12/2003

OTHER PUBLICATIONS

Bhattacharya et al., PLoS One 12(3): e0171355. https://doi.org/10.1371/journal.pone.0171355; 22 pages total (Year: 2017).*
Fenton et al., Medicinal Chemistry Research (2020) 29:1133-1146 (Year: 2020).*
Pucci et al., Current Opinion in Structural Biology 2022, 72: 161-168 (Year: 2022).*
Pak et al., PLoS One 18(3): e0282689. https://doi.org/10.1371/journal.pone.0282689 (Year: 2023).*
Antoine Gardin and Giuseppe Ronzitti, Archives de Pédiatrie 30 (2023) 8S46-8S52 (Year: 2023).*
Wang et al., Mol. Cell. Biol. (1990); 10 (12), 6781-6784 (Year: 1990).*
Chen et al., "Platelet-Derived Growth Factors and their Receptors: Structural and Functional Perspectives," *Biochim Biophys Acta*, vol. 1834:2176-2186, 2013.
International Search Report and Written Opinion for PCT/US2020/050903, dated Mar. 8, 2021 (17 pages).
Park et al., "Engineered Receptors for Human Cytomegalovirus that are Orthogonal to Normal Human Biology," *PLoS Pathog.*, vol. 16:e1008647, 2020.
Stegmann et al., "A Derivative of Platelet-Derived Growth Factor Receptor Alpha Binds to the Trimer of Human Cytomegalovirus and Inhibits Entry into Fibroblasts and Endothelial Cells," *PLoS Pathog.*, vol. 13:e1006273, 2017.
Velghe et al., "PDGFRA Alterations in Cancer: Characterization of a Gain-of-Function V536E Transmembrane Mutant as well as Loss-of-Function and Passenger Mutations," *Oncogene*, vol. 33:2568-2576, 2014.
Anonymous, "Predicted: platelet-derived growth factor receptor alpha [Bos indicus]" GenBank Accession No. XP_019818324, 2017 (2 pages).
Extended European Search Report for European Patent Application No. 20866261.9, dated Sep. 22, 2023 (13 pages).
Feldmann et al., "Targeted mutagenesis on PDGFRα-Fc identifies amino acid modifications that allow efficient inhibition of HCMV infection while abolishing PDGF sequestration," *PLoS Pathog.* 17(3):e1009471, 2021 (32 pages).
Torrente et al., "Mechanisms of PDGFRalpha promiscuity and PDGFRbeta specificity in association with PDGFB," *Frontiers in Biosci.* 7:434-446, 2015.

* cited by examiner

*Primary Examiner* — Christina M Borgeest
(74) *Attorney, Agent, or Firm* — Klarquist Sparkman, LLP

(57) ABSTRACT

Modified platelet-derived growth factor receptor alpha (PDGFRα) polypeptides are described. The modified polypeptides include at least one amino acid substitution that allows the polypeptide to retain the capacity to bind a cytomegalovirus (CMV) trimer comprised of glycoprotein H (gH), gL and gO, but leads to reduced binding to one or more platelet-derived growth factor (PDGF) ligands. Use of the modified PDGFRα polypeptides for inhibiting CMV replication and/or spread, or treating a CMV infection, is also described.

14 Claims, 13 Drawing Sheets

Specification includes a Sequence Listing.

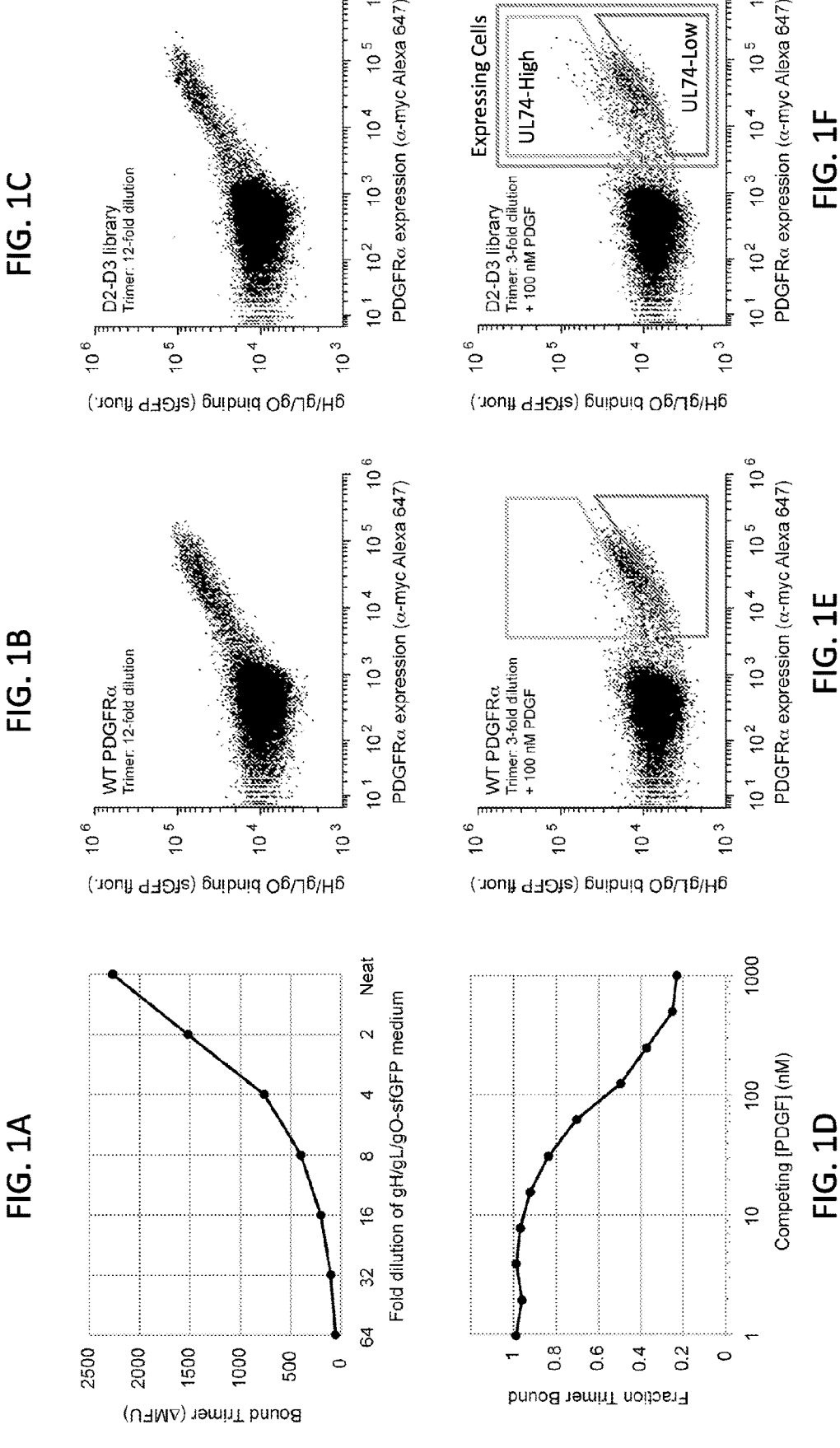

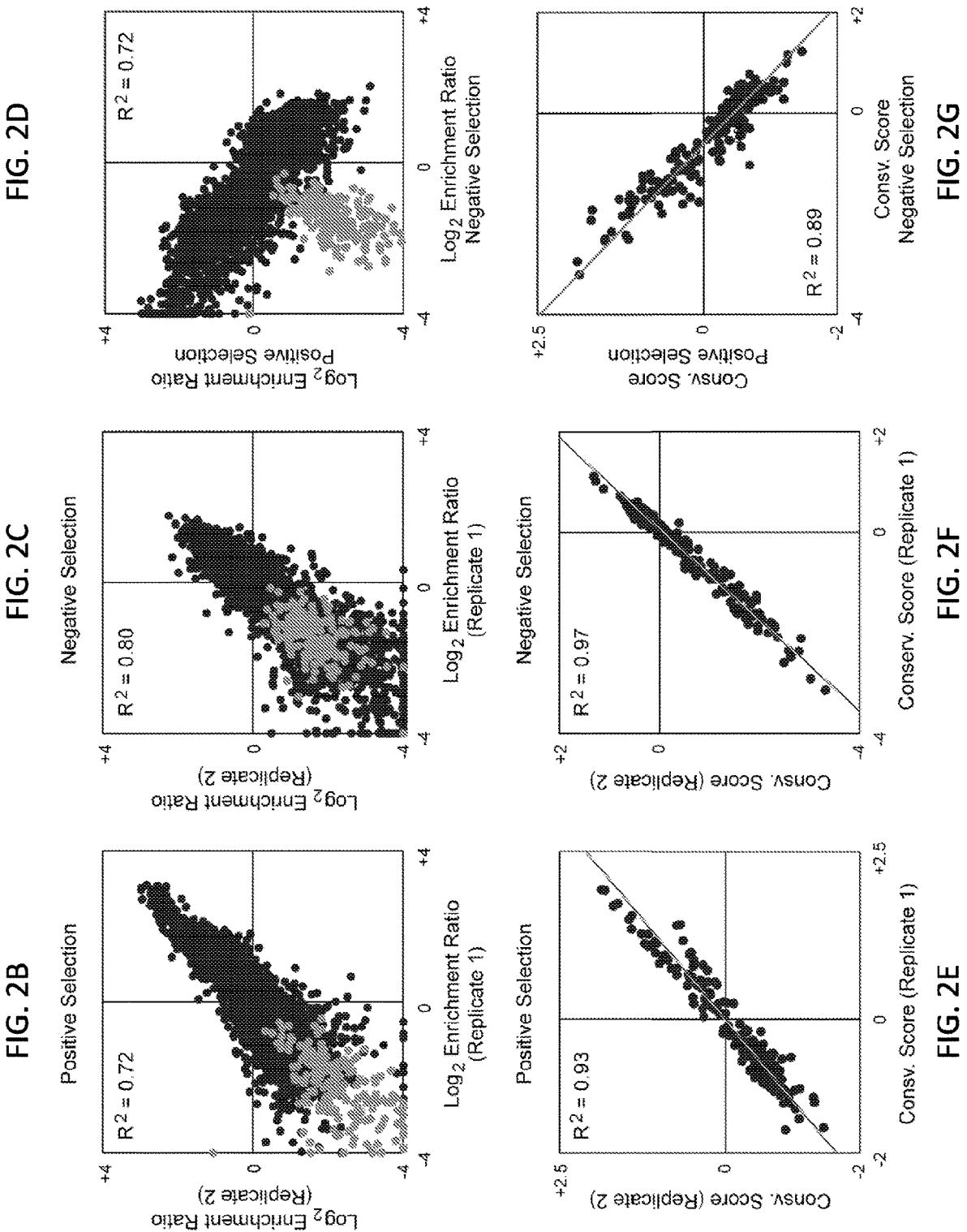

Surface

Cross Section

Log₂ Enrichment Ratio

-3 (depleted)     +3 (enriched)

R² = 0.43

Connectivity (Residues within 12 Å)

Consvervation Score (UL74-High sort)

|  | PDGFRα | Linker | IgG1-Fc |
|---|---|---|---|
| "Legacy": | Gln24-Glu524 | IEGRMD | PKSCDKTH...Lys447 |
| Redesign: | Gln24-Glu524 | GGGS | ----DKTH...Lys447 |

250 kD
150
100
75
50
37
25
20

WT
Y206S
V242K

Elution Volume (ml)

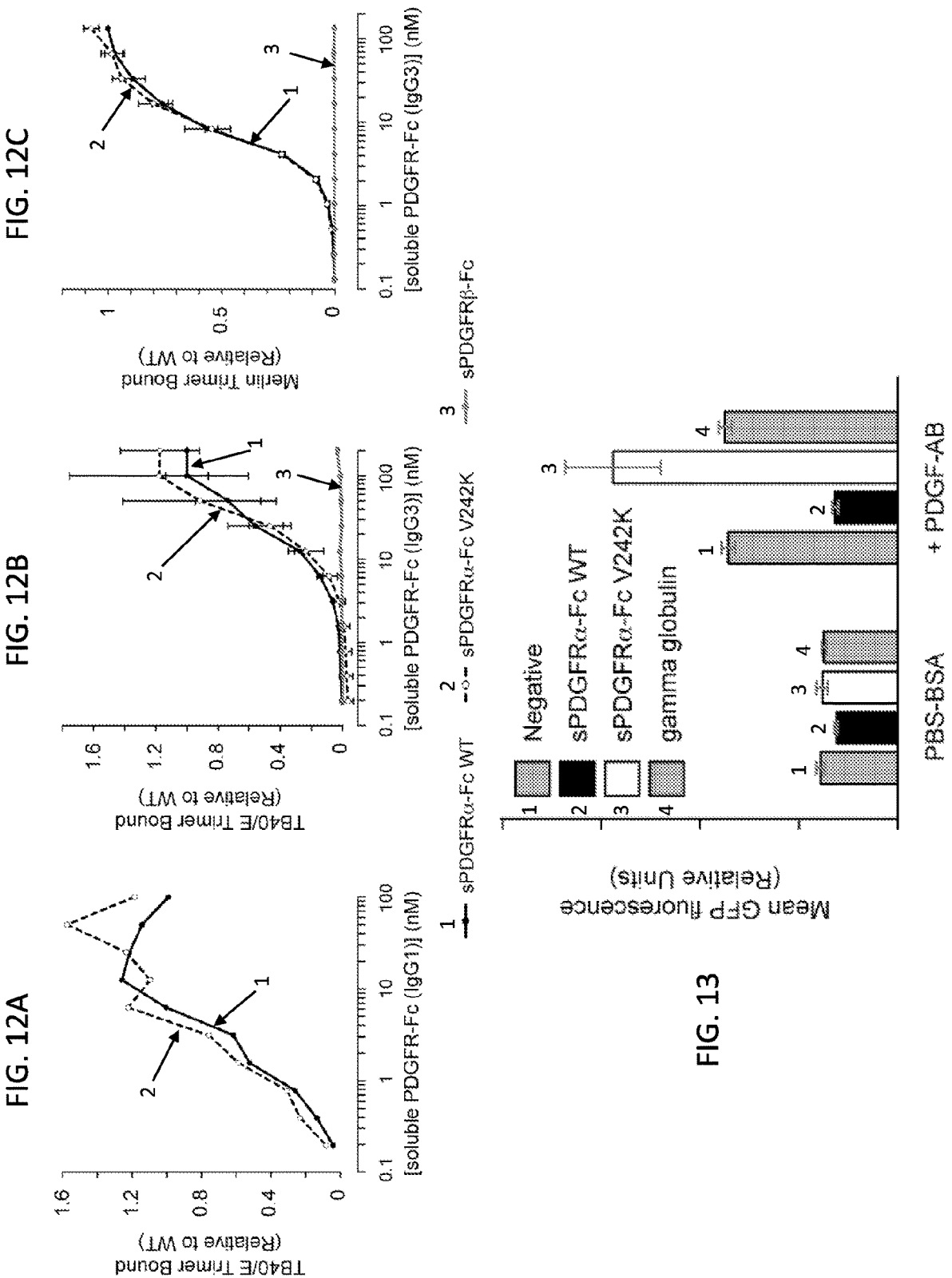

ENGINEERED RECEPTORS FOR HUMAN CYTOMEGALOVIRUS AND USES THEREOF

CROSS REFERENCE TO RELATED APPLICATIONS

This application is the U.S. National Stage of International Application No. PCT/US2020/050903, filed Sep. 15, 2020, which was published in English under PCT Article 21(2), which claims the benefit of U.S. Provisional Application No. 62/901,397, filed Sep. 17, 2019, which is herein incorporated by reference in its entirety.

FIELD

This disclosure concerns modified platelet-derived growth factor receptor a (PDGFRα) proteins that retain binding to the cytomegalovirus gH/gL/gO trimer, but exhibit reduced binding to PDGF ligands and methods of their use, particularly for inhibiting replication of cytomegalovirus.

BACKGROUND

Human cytomegalovirus (CMV; or human herpesvirus 5, HHV-5) is a ubiquitous pathogen that has infected most of the global adult population at some point, and typically causes asymptomatic infections that go unnoticed (Cannon et al., *Rev Med Virol.* 2010 July; 20(4):202-213; Staras et al., *Clin Infect Dis.* 2006 Nov. 1; 43(9):1143-1151). In some cases, individuals will experience mononucleosis-like symptoms, and severe disease can occur in immunocompromised or immunosuppressed adults (Emery, *J Clin Pathol.* 2001 February; 54(2):84-88). CMV infection may also have an oncomodulatory effect and is associated with tumor progression, most notably in glioblastoma (Cobbs et al., *Cancer Res.* 2002 Jun. 15; 62(12):3347-3350; Mitchell et al., *Neuro-oncology.* 2008 February; 10(1):10-18; Scheurer et al., *Acta Neuropathol.* 2008 July; 116(1):79-86; Michaelis et al., *Neoplasia.* 2009 January; 11(1):1-9). However, it is amongst pregnant women and newborns that CMV poses an outsized impact on public health (Cannon and Davis, *BMC Public Health.* 4 ed. 2005 Jun. 20; 5(1):70). Just over 1 in 200 infants born in the United States have congenital infection, and approximately one-fifth of these infants will suffer life-long neurological complications (Dollard et al., *Rev Med Virol.* 2007 September; 17(5):355-363; Kenneson and Cannon, *Rev Med Virol.* 2007 July; 17(4):253-276), which can include hearing and vision loss, seizures, behavioral disorders, and developmental delays (Grosse et al., *J Clin Virol.* 2008 February; 41(2):57-62; Suzuki et al., *Brain Dev.* 2008 June; 30(6):420-424; Zhang et al., *J Clin Virol.* 2007 November; 40(3):180-185; Coats et al., *J AAPOS.* 2000 April; 4(2):110-116; Gentile et al., *In Vivo.* 2017 May; 31(3):467-473). Ideally, infection during pregnancy would be avoided, but this is challenging. The high prevalence of CMV (especially in families with young children (Staras et al., *J Clin Virol.* 2008 November; 43(3) 266-271; Lanzieri et al., *Clin Vaccine Immunol.* 2015 February; 22(2):245-247)), easy transmission through contact with bodily fluids, recurrence of latent endogenous infections (Dupont and Reeves, *Rev Med Virol.* 2016 March; 26(2):75-89), reinfection by different exogenous strains (Ross et al., *J Infect Dis.* 2010 Feb. 1; 201(3):386-389), and difficulties recognizing asymptomatic infected individuals, mean that preventing virus spread is often impractical. Furthermore, antivirals have not been approved by the U.S. Food and Drug Administration for routine use in the treatment of congenital CMV where there are unique concerns regarding toxicity, and drug resistance is widely reported (Lurain and Chou, *Clin Microbiol Rev.* 2010 October; 23(4): 689-712). Faced with this reality, the American College of Obstetricians and Gynecologists does not make any specific recommendations for counseling or treating pregnant women for the prevention of CMV (American College of Obstetricians and Gynecologists. Practice bulletin no. 151: Cytomegalovirus, parvovirus B19, varicella zoster, and toxoplasmosis in pregnancy. *Obstetrics and gynecology.* 2015. p. 1510-1525). Thus, a need exists for an effective antiviral therapeutic for the prevention and treatment of CMV.

SUMMARY

Described herein are modified human PDGFRα polypeptides that retain the capacity to bind a cytomegalovirus (CMV) trimer comprised of glycoprotein H (gH), gL and gO, but exhibit reduced binding to one or more platelet-derived growth factor (PDGF) ligands, such as PDGF-AA, PDGF-AB, PDGF-BB and/or PDGF-CC. The modified polypeptides can be used as diagnostic or therapeutic agents for the detection, prophylaxis, or treatment of CMV infection.

Provided herein are modified PDGFRα polypeptides that include a human PDGFRα or an extracellular fragment thereof. The polypeptides comprise at least one amino acid substitution relative to wild-type human PDGFRα, and retain the capacity to bind a CMV trimer comprised of gH, gL and gO (or exhibit increased binding to the trimer), but exhibit reduced binding (or do not bind) to one or more PDGF ligands. In some embodiments, the at least one amino acid substitution is selected from any of the substitutions shown in Table 1. In some examples, the at least one amino acid substitution is a residue located at the binding interface of PDGFRα and PDGF.

Also provided herein are fusion proteins that include a modified PDGFRα polypeptide disclosed herein and a heterologous polypeptide. In some embodiments, the heterologous polypeptide is an Fc protein or a protein that can be used as a diagnostic/detection reagent, such as a fluorescent protein (for example, GFP) or an enzyme.

Further provided is an in vitro method of inhibiting CMV replication by contacting the CMV with a modified PDGFRα polypeptide or fusion protein disclosed herein. Methods of inhibiting CMV replication and/or spread in a subject are also provided. In some embodiments, the method includes administering to the subject a therapeutically effective amount of a modified PDGFRα polypeptide or fusion protein disclosed herein. Also provided is a method of treating a CMV infection in a subject by administering to the subject a therapeutically effective amount of a modified PDGFRα polypeptide or fusion protein disclosed herein.

Also provided are nucleic acid molecules and vectors that encode a modified PDGFRα polypeptide or fusion protein disclosed herein. Methods of inhibiting CMV replication and/or spread (or treating a CMV infection) in subject by administering the nucleic acid molecule or vector are further provided.

The foregoing and other objects and features of the disclosure will become more apparent from the following detailed description, which proceeds with reference to the accompanying figures.

BRIEF DESCRIPTION OF THE DRAWINGS

FIGS. 1A-1F: A selection strategy for identifying PDGFRα mutants selective for the CMV trimer. (FIG. 1A)

Expi293F cells expressing PDGFRα were incubated with dilutions of gH/gL/gO-superfolder GFP (sfGFP)-containing medium, and binding (shown as change in mean fluorescence units, ΔMFU) was measured by flow cytometry. (FIGS. 1B and 1C) Cells were transfected with wild-type (WT) PDGFRα (FIG. 1B) or the D2-D3 site-saturation mutagenesis (SSM) library (FIG. 1C) under conditions where typically no more than a single sequence variant is expressed by any given cell. Under these conditions, most cells are negative for PDGFRα expression. Cells were incubated with a subsaturating (12-fold) dilution of gH/gL/gO-sfGFP medium and analyzed by flow cytometry. (FIG. 1D) Cells were co-incubated with a 2-fold dilution of gH/gL/gO-sfGFP medium and different concentrations of PDGF (an equimolar mixture of PDGF-AA, AB, BB, and CC). The fluorescent signal of gH/gL/gO-sfGFP binding was compared to a sample without competing PDGF. (FIGS. 1E and 1F) Cells expressing WT PDGFRα (FIG. 1E) or the D2-D3 SSM library (FIG. 1F) were incubated with a 3-fold dilution of gH/gL/gO-sfGFP medium and 100 nM PDGF (25 nM of each subtype). During sorting of the D2-D3 library, the top 15% of PDGFRα-expressing cells that bind trimer were collected (UL74-High sort). Simultaneously, the bottom 15% of PDGFRα-expressing cells that bind trimer were also collected (UL74-Low sort).

FIGS. 2A-2G: A deep mutational scan of PDGFRα D2-D3 domains for CMV trimer interactions in the presence of PDGFs. (FIG. 2A) $\log_2$ enrichment ratios for individual mutations in the UL74-High sort are plotted from −3 (depleted) to +3 (enriched). Amino acid position is on the horizontal axis, and substitutions are on the vertical axis. *, stop codon. (FIG. 2B) Agreement between $\log_2$ enrichment ratios from independent replicates of the UL74-High sort (positive selection). $R^2$ values were calculated for nonsynonymous mutations and nonsense mutations. (FIG. 2C) Agreement between $\log_2$ enrichment ratios from replicates of the UL74-Low sort (negative selection). (FIG. 2D) $\log_2$ enrichment ratios for nonsynonymous mutations were anticorrelated between the negative and positive selections. Nonsense mutations were depleted from both sorts due to lost surface expression. (FIGS. 2E-2G) High correlation between conservation scores (calculated by averaging the $\log_2$ enrichment ratios for all nonsynonymous mutations at a given amino acid position) from independent replicates of the UL74-High (FIG. 2E) and UL74-Low (FIG. 2F) sorts. Conservation scores were anticorrelated between the two sorted populations (FIG. 2G).

(FIG. 3A) Model of PDGFRα D2-D3 domains bound to PDGF-BB (protruding subunit $B_1$, receding subunit B2). Conservation scores from the UL74-High sort are mapped to the PDGFRα surface, showing residues where mutations tend to be depleted, and residues where mutations tend to be enriched. (FIG. 3B) A cross section through PDGFRα highlights that enriched mutations are concentrated in the protein interior/core. (FIGS. 3C-3E) $\log_2$ enrichment ratios for individual mutations from the UL74-High sort are plotted from −3 (depleted) to +3 (enriched). Amino acid substitutions are indicated on the vertical axis, * is stop codon. The wild-type amino acid is black. Structural views are shown at right. Regions shown are the D2 core (FIG. 3C), PDGF-BB interface (FIG. 3D), and PDGF-BB interface and underlying D3 core (FIG. 3E).

(FIG. 4A) Expi293F cells expressing wild-type PDGFRα were co-incubated without or with competing PDGFs, and binding of TB40/E trimer (1/3 dilution of medium containing gH/gL/gO-sfGFP) was assessed by flow cytometry. Cells were gated (box) to compare binding at equivalent receptor expression levels. (FIG. 4B) Binding of TB40/E trimer to PDGFRα variants. Data are mean±SD, n=3. (FIG. 4C) Cells expressing PDGFRα variants were incubated with Merlin gH/gL/gO-sfGFP containing medium (1/3 dilution) in the absence or presence of PDGFs. Data are mean±SD, n=4.

(FIG. 5A) Flow cytometry analysis of mock-transfected Expi293F cells, or cells transfected with a plasmid driving myc-tagged PDGFRα expression and carrying a SRE-regulated GFP reporter. Signaling activity was quantified by measuring mean GFP fluorescence (vertical axis) of responsive cells in the gate (boxed). Shown are background PDGFRα signaling (left), PDGF-BB stimulated expression (center), and inhibition of PDGF-BB stimulation by sPDGFRα-Fc (right). (FIG. 5B) Stimulation of transfected Expi293F cells with 5 nM PDGF ligands. PDGF ligands were pre-incubated with 0.2% BSA (negative) or with a 3-fold molar excess of wild-type sPDGFRα-Fc, sPDGFRα-Fc Y206S, or sPDGFRα-Fc V242K. Data are mean±SD, n=3 independent replicates.

(FIG. 10A) The extracellular domain of PDGFRα (Gln24-Glu524) was fused via a short linker (IEGRMD, SEQ ID NO: 9; or GGGS, SEQ ID NO: 10) to the Fc region of IgG1 (PKSCDKTH, residues 225-232 of SEQ ID NO: 11; or DKTH, residues 229-232 of SEQ ID NO: 11). The "Legacy" sequence corresponds to the commercially supplied protein (R&D Systems) used in prior publications. The sequence was redesigned for this study. (FIG. 10B) Coomassie-stained SDS gel (run under denaturing and reducing conditions) of wild-type sPDGFRα-Fc eluted from a protein A column. The monomeric protein MW is predicted to be 82 kD. Additional weight may come from glycosylation and/or anomalous electrophoretic mobility. (FIG. 10C) SEC elution of wild-type, Y206S and V242K sPDGFRα-Fc. UV absorbance (y-axis) is scaled.

(FIG. 11A) Engineered orthogonal receptor sPDGFRα-Fc V242K was incubated at 40° C. for 7 days in 20 mM Tris pH 8.5 with 10 mM EDTA to promote Asn deamidation, or at 40° C. for 14 days in 50 mM sodium acetate pH 5.5 to promote Asn isomerization. The control sample in PBS (pH 7.4) was flash frozen and stored at −80° C. until analysis. SDS-polyacrylamide gel electrophoresis with Coomassie blue staining showed chemical instability of sPDGFRα-Fc V242K in the harsher pH 5.5 stress test. (FIG. 11B) Stressed proteins were analyzed by SEC on a Superdex 200 Increase 10/300 GL column with PBS pH 7.4 as the running buffer.

FIGS. 12A-12C: Soluble PDGFRα-Fc V242K binds HCMV trimer with comparable affinity to wild-type sPDGFRα-Fc. (FIG. 12A) Data were replicated using independent preparations of sPDGFRα WT (solid line) and V242K (dashed line) fused to the Fc region of IgG1. Binding to Expi293F cells expressing full-length gH, gL and gO from the HCMV TB40/E strain was assessed by flow cytometry. (FIGS. 12B and 12C) Soluble PDGFRα WT (solid line) and V242K (broken line) were purified as fusions to the Fc region of IgG3, matching the redesigned linker described in FIG. 6A. Binding to trimer from (FIG. 12B) TB40/E and (FIG. 12C) Merlin strains expressed on Expi293F cells was measured by flow cytometry. Data are mean±SD, n=3 (sPDGFRα-Fc WT and V242K) or 2 (sPDGFRβ-Fc).

FIG. 13: Gamma globulin has no effect on PDGF signaling in culture. PDGF signaling was assessed in Expi293F cells transiently transfected with a PDGFRα reporter plasmid as outlined in FIG. 5A. A 3-fold molar excess of wild-type sPDGFRα-Fc blocks 5 nM PDGF-AB signaling. Orthogonal engineered sPDGFRα-Fc V242K does not block signaling and the mutation shows no interactions with PDGFs in competitive binding experiments (see FIG. 4). Furthermore, wild-type or mutant sPDGFRα-Fc up to 100 nM shows no binding to PDGFRα-positive cells, and unanticipated interactions between receptor chains were excluded. However, sPDGFRα-Fc V242K does cause an increase in signaling of PDGF-A ligands (AA and AB). A non-specific carrier effect in which the orthogonal receptor stabilizes the hydrophobic ligand in solution is suspected, especially because the more hydrophobic variant sPDGFRα-Fc Y206S promotes an even bigger increase in PDGF-A signaling (see FIG. 5B). Human gamma globulin at the same concentration has no effect in this assay. Data are mean±SD, n=2 independent replicates.

SEQUENCE LISTING

Figure 2A:
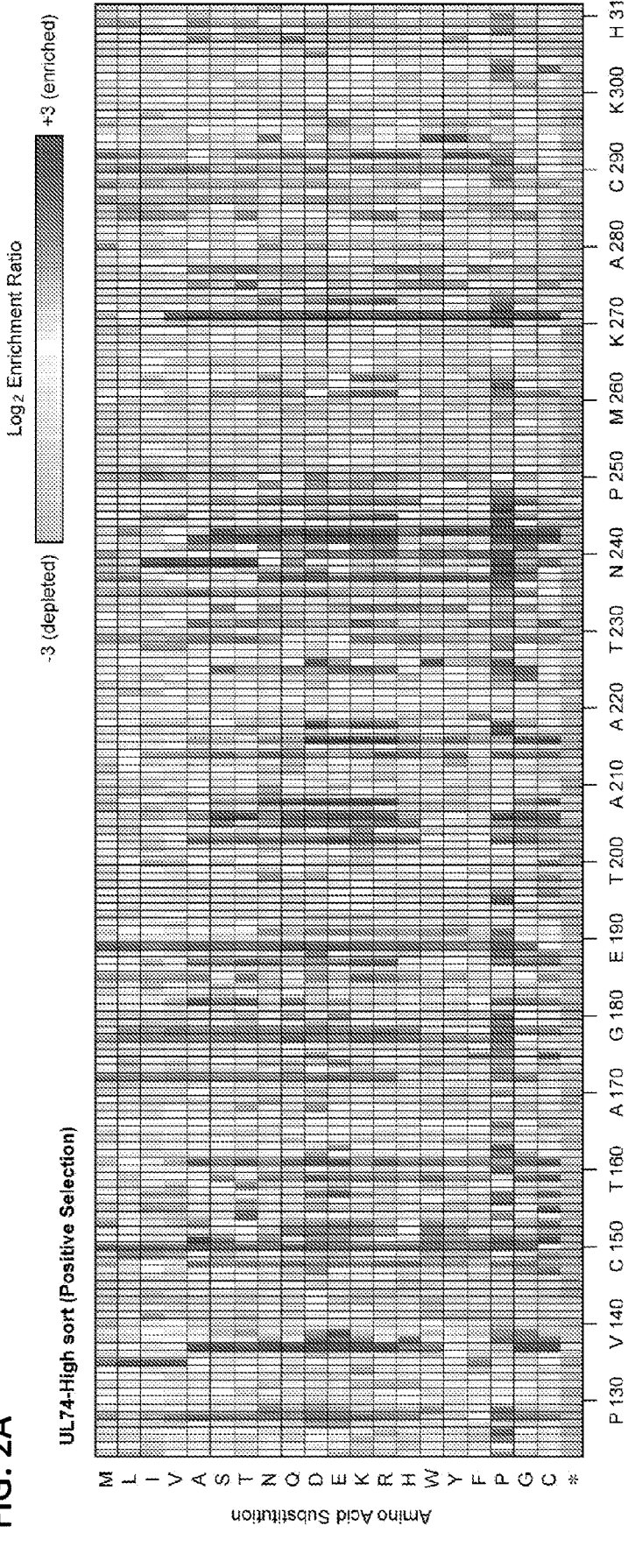
Figure 3A:
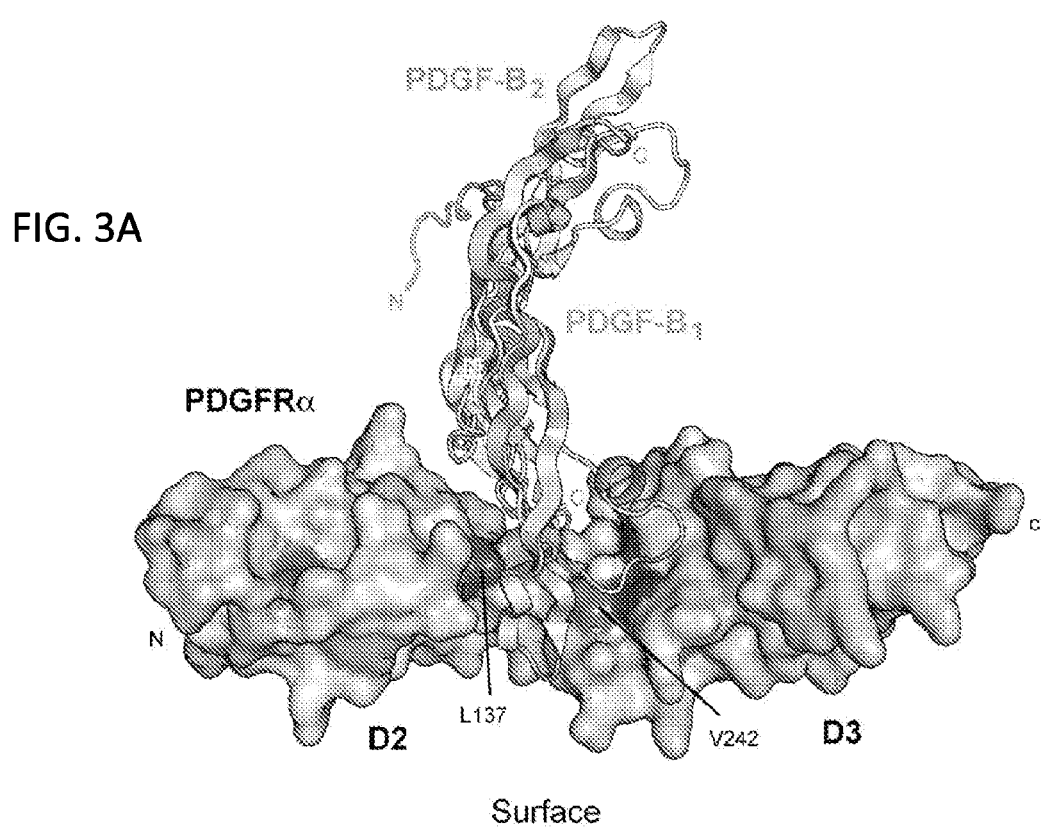
FIGS. 3A-3E: Hot spots in PDGFRα for mutations that increase CMV trimer binding in the presence of competing PDGFs.
Figure 3B:
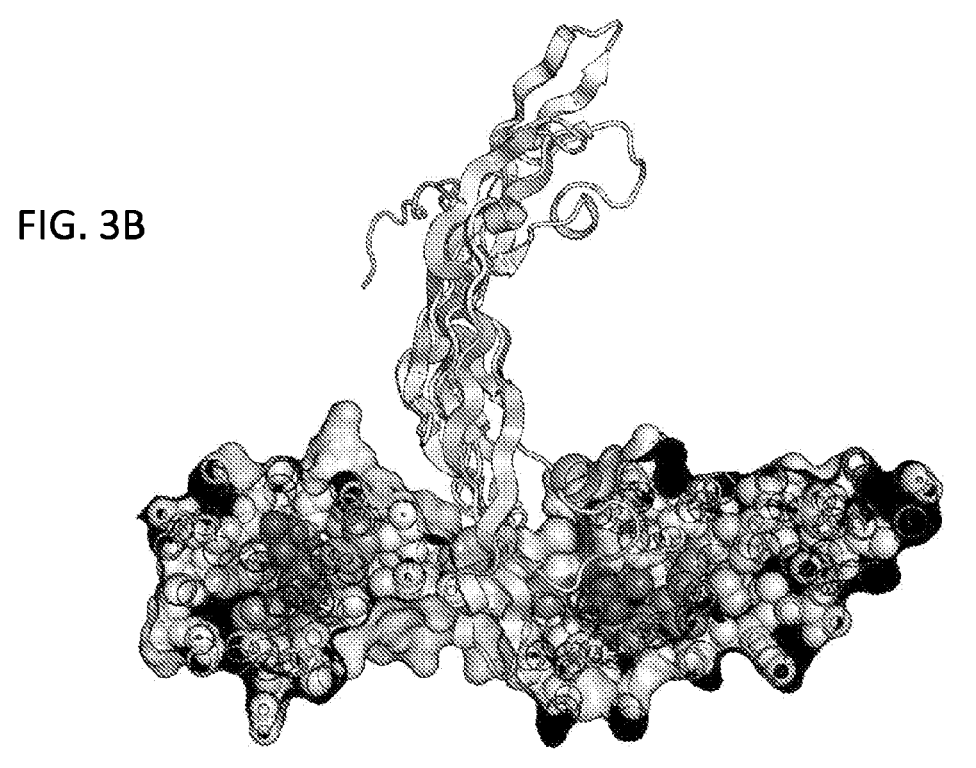
Figures 3C, 3D, 3E:
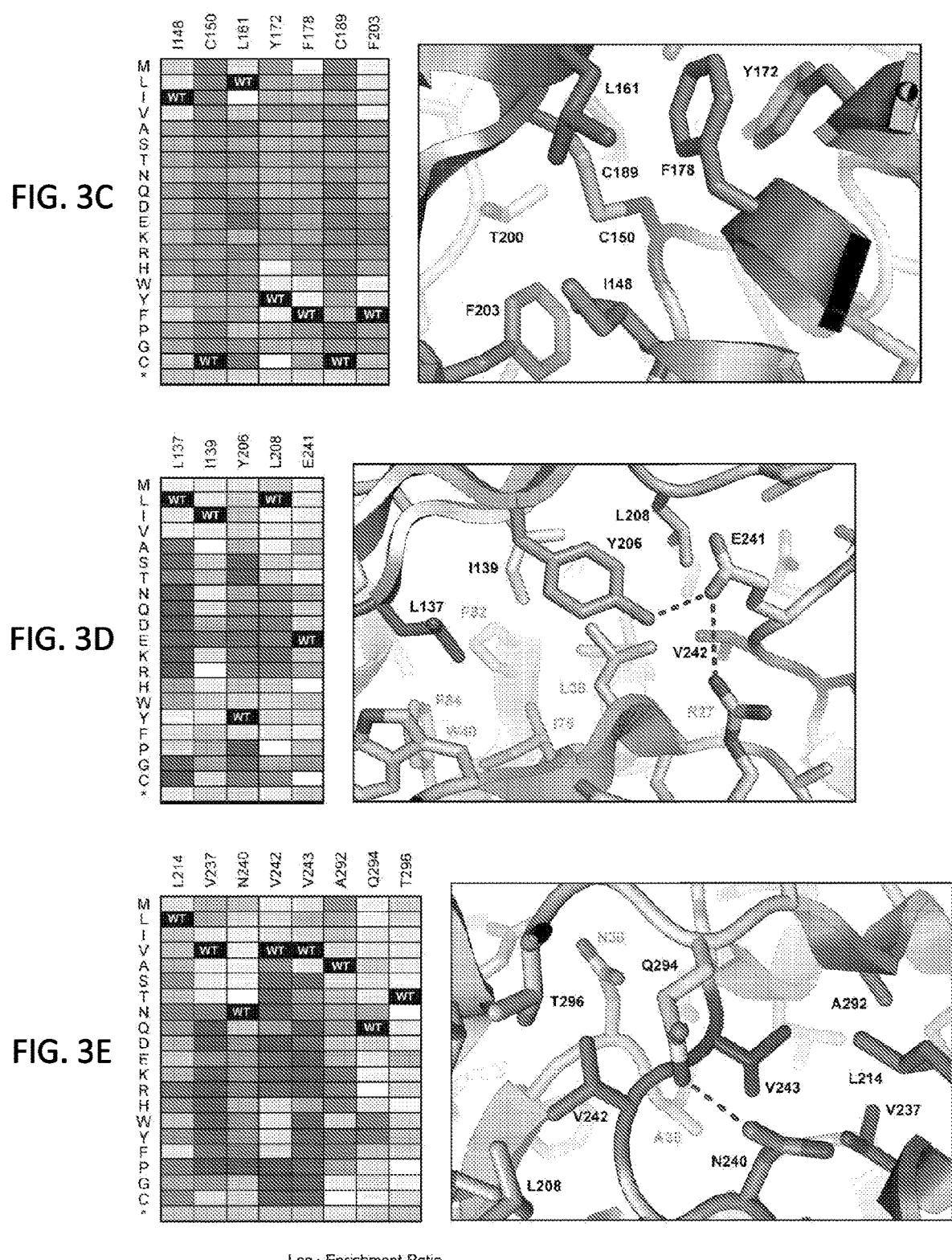

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 9, 2022, 62,500 bytes, which is incorporated by reference herein. In the accompanying sequence listing:

SEQ ID NO: 1 is the amino acid sequence of human PDGFRA isoform 1 (deposited under GenBank Accession No. NM_006206.4).

SEQ ID NO: 2 is the nucleotide sequence of human PDGFRA isoform 1 (deposited under GenBank Accession No. NM_006206.4).

SEQ ID NO: 3 is the amino acid sequence of glycoprotein O from CMV strain TB40/E (deposited under GenBank Accession No. ABV71596.1).

SEQ ID NO: 4 is the amino acid sequence of glycoprotein H from CMV strain TB40/E (deposited under GenBank Accession No. ABV71597.1).

SEQ ID NO: 5 is the amino acid sequence of glycoprotein L from CMV strain TB40/E (deposited under GenBank Accession No. ABV71629.1).

SEQ ID NO: 6 is the amino acid sequence of glycoprotein O from CMV strain Merlin (deposited under GenBank Accession No. AJY56739.1).

SEQ ID NO: 7 is the amino acid sequence of glycoprotein H from CMV strain Merlin (deposited under GenBank Accession No. YP_081523.1).

SEQ ID NO: 8 is the amino acid sequence of glycoprotein L from CMV strain Merlin (deposited under GenBank Accession No. YP_081555.1).

SEQ ID NO: 9 is the amino acid sequence of a peptide linker.

SEQ ID NO: 10 is the amino acid sequence of a peptide linker.

SEQ ID NO: 11 is the amino acid sequence of human IgG1 (deposited under GenBank KY432415.1).

SEQ ID NO: 12 is the amino acid sequence of a hemagglutinin (HA) leader sequence.

SEQ ID NO: 13 is the amino acid sequence of a peptide linker.

SEQ ID NO: 14 is the amino acid sequence of human PDGFRβ isoform 1 (deposited under GenBank NM_002609.3).

SEQ ID NO: 15 is the amino acid sequence of human IgG3 (deposited under GenBank P01860.2).

SEQ ID NO: 16 is the nucleotide sequence of a PDGFRA gene-specific oligonucleotide.

SEQ ID NO: 17 is the amino acid sequence of a fusion protein that includes the PDGFRα signal peptide and ectodomain, a linker and human IgG1 Fc.

DETAILED DESCRIPTION

I. Terms and Methods

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "a polypeptide" includes single or plural polypeptides and can be considered equivalent to the phrase "at least one polypeptide." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: To provide or give a subject an agent, such as a modified human PDGFR-α polypeptide, by any effective route. Exemplary routes of administration include, but are not limited to, oral, injection (such as subcutaneous, intramuscular, intradermal, intraperitoneal, intratumoral, and intravenous), transdermal, intranasal, and inhalation routes.

Contacting: Placement in direct physical association; includes both in solid and liquid form.

CMV (cytomegalovirus): A genus of viruses in the family Herpesviridae and subfamily Betaherpesviriniae having a large (~230 kB) double-stranded DNA genome. In most people, CMV infection is asymptomatic, but this virus can cause severe disease in immunocompromised or immunosuppressed subjects. Additionally, CMV infection of newborns can cause life-long neurological complications (Dollard et al., *Rev Med Virol.* 2007 September; 17(5):355-363; Kenneson and Cannon, *Rev Med Virol.* 2007 July; 17(4): 253-276), including hearing and vision loss, seizures, behavioral disorders, and developmental delays (Grosse et al., *J Clin Virol.* 2008 February; 41(2):57-62; Suzuki et al., *Brain Dev.* 2008 June; 30(6):420-424; Zhang et al., *J Clin Virol.* 2007 November; 40(3):180-185; Coats et al., *J AAPOS.* 2000 April; 4(2):110-116; Gentile et al., *In Vivo.* 2017 May; 31(3):467-473). Human CMV is also known as human herpesvirus 5 (HHV-5). Human CMV expresses a trimeric glycoprotein complex comprised of gL, gH and gO, which is required for entry into fibroblasts cells, as well as a pentameric complex comprised of gH, gL, pUL128, pUL130 and pUL131A, which is required for entry into endothelial/epithelial cells.

Fusion protein: A protein comprising at least a portion of two different (heterologous) proteins. In some embodiments herein, a fusion protein includes a modified PDGFR-α polypeptide and a heterologous protein, such as an Fc protein.

Heterologous: Originating from a separate genetic source or species.

Pharmaceutically acceptable carriers: The pharmaceutically acceptable carriers of use are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the polypeptides and other compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional nontoxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Platelet-derived growth factor receptor alpha (PDGFRα): A cell-surface tyrosine kinase receptor for members of the PDGF growth factor family. Exemplary amino acid and nucleic acid sequences of human PDGFRα are publicly accessible, such as under NCBI Gene ID 5156 (for example, GenBank Accession No. NM_006206), and include the sequences set forth herein as SEQ ID NO: 1 (amino acid) and SEQ ID NO: 2 (nucleic acid).

Polypeptide, peptide and protein: Refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Replication: The ability of a virus to produce progeny, including mature infectious progeny. Methods that can be used to determine replication of a virus include but are not limited to infectious center assays, viral titer by TCID50 (tissue-culture infectious doses 50%) or plaque assay, replication in single-step growth curves, or expression measurement of viral nucleic acids or proteins.

Subject: Living multi-cellular vertebrate organisms, a category that includes both human and veterinary subjects, including human and non-human mammals.

Therapeutically effective amount: A quantity of a specific substance (such as a modified human PDGFR-α, polypeptide) sufficient to achieve a desired effect in a subject being treated. For instance, this can be the amount necessary to inhibit CMV replication or reduce CMV titer in a subject. In one embodiment, a therapeutically effective amount is the amount necessary to inhibit CMV replication by at least 10%, at least 20%, at least 30%, at least 40%, at least 50%, at least 60%, at least 70%, at least 80%, or at least 90% (as compared to the absence of treatment). In another embodiment, a therapeutically effective amount is the amount necessary to reduce CMV titer in a subject by at least 10%, at least 20%, at least 30%, at least 40%, at least 50%, at least 60%, at least 70%, at least 80%, or at least 90% (as compared to the absence of treatment). The therapeutically effective amount can also be the amount necessary to reduce or eliminate one of more symptoms of CMV infection, or reduce or eliminate transmission of CMV from a pregnant female to an infant. For example, in some embodiments, a therapeutically effect amount is the amount necessary to reduce the risk of transmission of CMV by at least 20%, at least 30%, at least 40%, at least 50%, at least 60%, at least 70%, at least 80%, or at least 90% (as compared to the absence of treatment).

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. In some embodiments, the vector is a virus vector, such as a lentivirus vector.

II. Introduction

The identification of platelet-derived growth factor receptor a (PDGFRα) as a CMV receptor has generated excitement towards the discovery of new therapeutics that inhibit virus-host cell attachment and entry. Two glycoprotein complexes on the CMV surface drive broad host cell tropism (Gerna et al., *Vaccines (Basel)*. 2019 Jul. 22; 7(3):70; Sinzger et al., *Curr Top Microbiol Immunol*. 2008; 325:63-83). A pentameric complex of glycoprotein H (gH; UL75), gL (UL115), UL128, UL130 and UL131A mediates entry into epithelial and endothelial cells (Hahn et al., *J Virol*. 2004 September; 78(18):10023-10033; Wang and Shenk, *Proc Natl Acad Sci USA*. 2005 Dec. 13; 102(50):18153-18158; Wang and Shenk, *J Virol*. 2005 August; 79(16):10330-10338; Ryckman et al., *Proc Natl Acad Sci USA*. 2008 Sep. 16; 105(37):14118-14123; Ryckman et al., *J Virol*. 2008 January; 82(1):60-70; Adler et al., *J Gen Virol*. 2006 September; 87(Pt 9):2451-2460), possibly through engagement of neuropilin-2 (Martinez-Martin et al., *Cell*. 2018 Aug. 23; 174(5):1158-1171.e19) or the olfactory receptor OR14I1 (Xiaofei et al., *Proc Natl Acad Sci USA*. 2019 Apr. 2; 116(14):7043-7052) on the host cell.

A trimeric complex of gH, gL and gO (UL74) is sufficient for CMV entry into fibroblasts, and is also necessary for entry into other cell types by promoting membrane fusion (Huber and Compton, *J Virol*. 1998 October; 72(10):8191-8197; Huber and Compton, *J Virol*. 1999 May; 73(5):3886-3892; Zhou et al, *J Virol*. 2015 September; 89(17):8999-9009). Multiple lines of evidence indicate that PDGFRα is the receptor for the trimer. Decreased PDGFRα expression reduces CMV entry into fibroblasts (Kabanova et al., *Nat Microbiol*. 2016 Jun. 6; 1(8):16082; Soroceanu and Akhavan, *Nature*. 2008 Sep. 18; 455(7211):391-395; Wu et al., *PLoS Pathog*. 2017 April; 13(4):e1006281; Wu et al., *Proc Natl Acad Sci USA*. 2018 Oct. 16; 115(42):E9889—E9898); gO can specifically bind PDGFRα-expressing cells (Wu et al., *PLoS Pathog*. 2017 April; 13(4):e1006281); a quaternary complex of soluble extracellular regions (gH-gL-gO-PDGFRα) can be purified in vitro and the components bind with high nanomolar affinity (Martinez-Martin et al., *Cell*. 2018 Aug. 23; 174(5):1158-1171.e19; Kabanova et al., *Nat Microbiol*. 2016 Jun. 6; 1(8):16082); CMV strains lacking the trimer do not use PDGFRα to infect cells (Wu et al., *PLoS Pathog*. 2017 April; 13(4):e1006281; Stegmann et al., *PLoS Pathog*. 2017 April; 13(4):e1006273); and the extracellular domain of PDGFRα blocks virus entry (Martinez- Martin et al., *Cell*. 2018 Aug. 23; 174(5):1158-1171.e19; Wu et al., *PLoS Pathog*. 2017 April; 13(4):e1006281; Stegmann et al., *PLoS Pathog*. 2017 April; 13(4):e1006273). This has led to the soluble domain of PDGFRα or derivative fragments thereof being explored as antiviral biological agents (Wu et al., *PLoS Pathog*. 2017 April; 13(4):e1006281; Stegmann et al., *PLoS Pathog*. 2017 April; 13(4):e1006273), as any mutations in CMV to escape receptor-based inhibitors would likely decrease binding to the natural receptor and attenuate virulence. Soluble PDGFRα ectodomain effectively blocks virus entry whether applied pre- or post-cell attachment, due to inhibition of both early attachment and fusion steps (Wu et al., *PLoS Pathog*. 2017 April; 13(4):e1006281; Stegmann et al., *PLoS Pathog*. 2017 April; 13(4):e1006273). Furthermore, soluble PDGFRα inhibits cell entry at low concentrations when only a minor fraction of glycoprotein trimer is bound, and blocks entry by multiple CMV strains that express both trimer and pentamer complexes (Wu et al., *PLoS Pathog*. 2017 April; 13(4):e1006281; Stegmann et al., *PLoS Pathog*. 2017 April; 13(4):e1006273).

While appealing, the use of soluble PDGFRα to treat CMV in a human patient comes with associated risks. PDGFRα is an important receptor for platelet-derived growth factors (PDGFs), and regulates cellular proliferation, differentiation and development of multiple tissues during embryogenesis and onwards through adulthood (Andrae et al., *Genes Dev*. 2008 May 15; 22(10):1276-1312). The PDGF ligands are small polypeptides that covalently associate in disulfide-bonded homo- and heterodimers, which display differing activities towards PDGFRα and its close relative PDGFRβ (Chen et al., *Biochim Biophys Acta*. 2013 October; 1834(10):2176-2186). Four ligands interact with PDGFRα with high affinity—PDGF-AA, AB, BB, and CC (Fretto et al., *J Biol Chem*. 1993 Feb. 15; 268(5):3625-3631; Li et al., *Nat Cell Biol*. 2000 May; 2(5):302-309)—and bind two receptor chains at opposing ends to form a receptor-ligand dimer-receptor signaling complex (Shim et al., *Proc Natl Acad Sci USA*. 2010 Jun. 22; 107(25):11307-11312; Chen et al., *J Mol Biol*. 2015 Dec. 4; 427(24):3921-3934). PDGFs compete with the CMV trimer for PDGFRα binding and block infection (Soroceanu and Akhavan, *Nature*. 2008 Sep. 18; 455(7211):391-395; Wu et al., *PLoS Pathog*. 2017 April; 13(4):e1006281), indicating that either there is steric hinderance, the respective interaction sites are at least partially overlapping, or binding-induced conformational effects are incompatible with multiple ligands binding simultaneously. Treatment with soluble PDGFRα therefore risks disrupting essential physiological signaling with potentially severe consequences for a developing infant, while sequestration of the administered protein by endogenous PDGFs will further limit efficacy. Ideally, mutations in the receptor will exist that knock out PDGF interactions while keeping intact the site or sites engaged by CMV.

A high resolution crystal structure of PDGF-BB-bound PDGFRβ has illuminated atomic details of ligand-receptor interactions in the family, revealing a predominantly hydrophobic interface at the crevice between the second (D2) and third (D3) extracellular domains of the receptor (Shim et al., *Proc Natl Acad Sci USA*. 2010 Jun. 22; 107(25):11307-11312). However, the binding site for gO is ambiguous. Cryo-electron microscopy suffers from conformational diversity and low resolution (Kabanova et al., *Nat Microbiol*. 2016 Jun. 6; 1(8):16082); PDGFRα peptide fragment analysis failed to discover any one peptide solely responsible for high affinity binding (Stegmann et al., *PLoS Pathog*. 2017 April; 13(4):e1006273); and while domain deletions have shown PDGFRα-D3 is important (Wu et al., *Proc Natl Acad Sci USA*. 2018 Oct. 16; 115(42):E9889—E9898), such studies have coarse resolution. The absence of detailed structural information on the CMV trimer-PDGFRα complex means the engineering of CMV-specific receptors orthogonal to human biology remains an unmet need.

The present disclosure solves this problem through the use of mutagenesis and in vitro selection. By tracking the enrichment or depletion of sequence variants in a diverse library using next generation sequencing, the relative phenotypes of thousands of mutations can be simultaneously assessed in a single experiment, referred to as deep mutagenesis (Fowler and Fields, *Nat Methods*. 2014 August; 11(8):801-807). Deep mutational scans have been used to address and engineer specificity in proteins that promiscuously bind multiple ligands (Berger et al., *Elife*. 2016 Nov. 2; 5:1422; Procko et al., *Cell*. 2014 Jun. 19; 157(7):1644-1656; Wrenbeck et al., *Nat Commun*. 2017 Jun. 6; 8(1):15695), and methods for deep mutagenesis of membrane proteins expressed in human cells have been optimized (Park et al., *J Biol Chem*. 2019; 294(13):4759-4774; Heredia et al., *J Immunol*. 2018 Apr. 20; 200(11):ji1800343-3839; Heredia et al., *J Virol*. 2019 Jun. 1; 93(11):e00219-19). By screening through all possible single amino acid substitutions in the D2-D3 domains, it was discovered that, unlike PDGF binding, CMV trimer interactions persist when PDGFRα conformation is disrupted by mutations within the folded core. And more relevant to therapeutic design, specific mutations are also identified on the PDGFRα surface that enhance trimer binding in the presence of high PDGF concentrations.

III. Overview of Embodiments

Described herein are modified human PDGFRα polypeptides that retain the capacity to bind a CMV trimer comprised of gH, gL and gO, but exhibit reduced binding to one or more PDGF ligands, such as PDGF-AA, PDGF-AB, PDGF-BB and/or PDGF-CC compared to wild type PDGFRα. In particular, provided herein are modified PDGFRα polypeptides that include a human PDGFRα or an extracellular fragment thereof. The polypeptides include at least one amino acid substitution relative to a wild-type human PDGFRα (such as isoform 1 of human PDGFRα set forth herein as SEQ ID NO: 1) and retain the capacity to bind a CMV trimer comprised of gH, gL and gO (or exhibit increased binding to the trimer), but exhibit reduced binding (or lack the ability to bind) to one or more PDGF ligands compared to wild type PDGFRα.

In some embodiments, the at least one (e.g., at least one, at least two, at least three, at least four, at least five, or more) amino acid substitution is selected from any of the substitutions shown in Table 1.

In some embodiments, the at least one amino acid substitution is a residue located at the binding interface of PDGFRα and PDGF. In some examples, the at least one amino acid substitution is at a residue corresponding to residue 137, 139, 185, 206, 208, 242, 261 or 271 of human PDGFRα of SEQ ID NO: 1. In specific non-limiting examples, the at least one amino acid substitution is selected from the group consisting of L137A, L137S, L137T, L137N, L137Q, L137D, L137E, L137K, L137R, L137G, L137C, I139E, G185K, G185R, Y206S, Y206T, Y206Q, Y206D, Y206E, Y206K, Y206R, Y206P, Y206G, Y206C, L208N, L208Q, L208D, L208E, L208K, L208R, L208C, V242A, V242S, V242T, V242N, V242Q, V242D, V242E, V242K, V242R, V242P, V242G, V242C, L261K, L261R, L261P, L261C, L271V, L271A, L271S, L271T, L271N, L271Q, L271D, L271E, L271K, L271R, L271H, L271W, L271Y, L271F, L271P, L271G and L271C, with reference to SEQ ID NO: 1. In particular non-limiting examples, the amino acid substitution is selected from the group consisting of L137K, L137Q, Y206S, V242K and V242T.

In some embodiments, the modified polypeptides contain only a single amino acid substitution relative to a wild-type human PDGFRα (such as isoform 1 of human PDGFRα set forth herein as SEQ ID NO: 1), such as one amino acid substitution listed in Table 1. In other examples, the modified polypeptides include two, three, four, five or more amino acid substitutions, such as two, three, four, five or more amino acid substitutions listed in Table 1. In specific examples, the modified polypeptide includes only a single substitution at residue 137, 139, 185, 206, 208, 242, 261 or 271 of human PDGFRα of SEQ ID NO: 1. In other specific examples, the modified polypeptide includes two, three, four or five amino acid substitutions at residues selected from the group consisting of residues 137, 139, 185, 206, 208, 242, 261 and 271 of human PDGFRα of SEQ ID NO: 1. In particular non-limiting examples, the single substitution is selected from the group consisting of L137K, L137Q, Y206S, V242K and V242T.

In some embodiments, the modified polypeptides are full-length human PDGFRα polypeptides. In some examples, the amino acid sequence of the polypeptide is at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8% or at least 99.9% identical to SEQ ID NO: 1 and includes at least one amino acid substitution disclosed herein.

In other embodiments, the modified polypeptides consist of an extracellular fragment of human PDGFRα. For example, the modified polypeptide can consist of the complete extracellular domain of human PDGFRα, such as domains D2 and D3, for example corresponding to amino acid residues 24-524 of SEQ ID NO: 1, or the modified polypeptides can consist of a portion of the extracellular domain, such as about 200 amino acids, about 250 amino acids, about 300 amino acids, about 350 amino acids, about 400 amino acids or about 450 amino acids of the extracellular domain. In some examples, the amino acid sequence of the extracellular fragment is at least 90%, at least 91%, at least 92%, at least 93%, at least 94%, at least 95% at least 96%, at least 97%, at least 98%, at least 99%, at least 99.1%, at least 99.2%, at least 99.3%, at least 99.4%, at least 99.5%, at least 99.6%, at least 99.7%, at least 99.8% or at least 99.9% identical to residues 24 to 524 of SEQ ID NO: 1 and includes at least one amino acid substitution disclosed herein.

Also provided are fusion proteins that include a modified PDGFRα polypeptide disclosed herein and a heterologous polypeptide. In some embodiments, the heterologous polypeptide is an Fc protein or a protein that can be used as a diagnostic/detection reagent, such as a fluorescent protein (for example, GFP) or an enzyme (for example, alkaline phosphatase, horse radish peroxidase or luciferase). In some embodiments, the heterologous polypeptide is an antibody or antigen-binding protein for avid binding to a second CMV antigen. In some embodiments, the heterologous polypeptide is an antibody or antigen-binding protein for tethering to cells or cellular surroundings (for example, to recruit immune cells). In some embodiments, the heterologous polypeptide is a cytokine, ligand or receptor for evoking a biological response. In some embodiments, the heterologous polypeptide is a protein that increases the serum half-life (for example, antibody Fc or serum albumin). In some examples, the heterologous polypeptide comprises an Fc protein, such as IgG1 Fc or a portion thereof. In specific examples, the fusion protein comprises or consists of SEQ ID NO: 17.

Compositions that include a modified PDGFRα polypeptide or fusion protein thereof and a pharmaceutically acceptable carrier are also provided.

Further provided is an in vitro method of inhibiting CMV replication by contacting the CMV with a modified PDGFRα polypeptide or fusion protein disclosed herein. In some examples, CMV-infected cells (such as cultured cell lines or primary cells) are contacted with the modified PDGFRα polypeptide, such as to test the effect of the modified polypeptide on CMV replication.

Methods of inhibiting CMV replication and/or spread in a subject are also provided. In some embodiments, the method includes administering to the subject a therapeutically effective amount of a modified PDGFRα polypeptide, fusion protein or composition disclosed herein. Also provided is a method of treating a CMV infection in a subject, comprising administering to the subject a therapeutically effective amount of a modified PDGFRα polypeptide, fusion protein, or composition disclosed herein. In some examples, the subject is a female subject who is pregnant. In some examples, the subject is an infant, such as an infant whose mother is positive for CMV. In some examples, the subject has an immunodeficiency or is immunosuppressed. In other examples, the subject is a transplant recipient.

Also provided are nucleic acid molecules and vectors that encode a modified PDGFRα polypeptide or fusion protein disclosed herein. In some examples, the nucleic acid molecules and vectors have different codon usage or may be codon optimized for expression in human cells. In some examples, the nucleic acid molecules and vectors encode different isoforms of PDGFRα polypeptide. In some examples, the nucleic acid molecules and vectors carry natural human polymorphisms.

Further provided are compositions that include a nucleic acid molecule or vector disclosed herein and a pharmaceutically acceptable carrier.

Methods of inhibiting CMV replication and/or spread in a subject by administering a therapeutically effective amount of a nucleic acid molecule, vector, or composition disclosed herein are further provided. Further provided are methods of treating a CMV infection in a subject, comprising administering to the subject a therapeutically effective amount of a nucleic acid molecule, vector or composition disclosed herein. In some examples, the subject is a female subject who is pregnant. In some embodiments, the subject is an infant, such as an infant whose mother is positive for CMV. In some examples, the subject has an immunodeficiency or is immunosuppressed. In other examples, the subject is a transplant recipient.

IV. Embodiments

Embodiment 1. A modified platelet-derived growth factor receptor alpha (PDGFRα) polypeptide, comprising a human PDGFRα or an extracellular fragment thereof, wherein the polypeptide comprises at least one amino acid substitution relative to wild-type human PDGFRα, and retains the capacity to bind a cytomegalovirus (CMV) trimer comprised of glycoprotein H (gH), gL and gO, but exhibits reduced binding to one or more platelet-derived growth factor (PDGF) ligands compared to wild type PDGFRα.

Embodiment 2. The modified polypeptide of embodiment 1, wherein the at least one amino acid substitution is a substitution selected from Table 1.

Embodiment 3. The modified polypeptide of embodiment 1 or embodiment 2, wherein the at least one amino acid substitution is a residue located at the interface of PDGFRα and PDGF.

Embodiment 4. The modified polypeptide of embodiment 3, wherein the at least one amino acid substitution is at residue 137, 139, 185, 206, 208, 242, 261 or 271 of human PDGFRα of SEQ ID NO: 1.

Embodiment 5. The modified polypeptide of embodiment 3 or embodiment 4, wherein the at least one amino acid substitution is selected from the group consisting of L137A, L137S, L137T, L137N, L137Q, L137D, L137E, L137K, L137R, L137G, L137C, I139E, G185K, G185R, Y206S, Y206T, Y206Q, Y206D, Y206E, Y206K, Y206R, Y206P, Y206G, Y206C, L208N, L208Q, L208D, L208E, L208K, L208R, L208C, V242A, V242S, V242T, V242N, V242Q, V242D, V242E, V242K, V242R, V242P, V242G, V242C, L261K, L261R, L261P, L261C, L271V, L271A, L271S, L271T, L271N, L271Q, L271D, L271E, L271K, L271R, L271H, L271W, L271Y, L271F, L271P, L271G and L271C, with reference to SEQ ID NO: 1.

Embodiment 6. The modified polypeptide of any one of embodiments 1-5, having a single amino acid substitution relative to human PDGFRα of SEQ ID NO: 1.

Embodiment 7. The modified polypeptide of embodiment 6, wherein the single amino acid substitution is selected from the group consisting of L137K, L137Q, Y206S, V242K and V242T.

Embodiment 8. The modified polypeptide of any one of embodiments 1-7, comprising full-length human PDGFRα.

Embodiment 9. The modified polypeptide of embodiment 8, wherein the amino acid sequence of the polypeptide is at least 95% identical to SEQ ID NO: 1.

Embodiment 10. The modified polypeptide of embodiment 8, wherein the amino acid sequence of the polypeptide is at least 99% identical to SEQ ID NO: 1.

Embodiment 11. The modified polypeptide of any one of embodiments 1-7, wherein the polypeptide consists of an extracellular fragment of human PDGFRα.

Embodiment 12. The modified polypeptide of embodiment 11, wherein the extracellular fragment corresponds to residues 24 to 524 of human PDGFRα.

Embodiment 13. The modified polypeptide of embodiment 11 or embodiment 12, wherein the amino acid sequence of the extracellular fragment is at least 95% identical to residues 24 to 524 of SEQ ID NO: 1.

Embodiment 14. The modified polypeptide of embodiment 11 or embodiment 12, wherein the amino acid sequence of the extracellular fragment is at least 99% identical to residues 24 to 524 of SEQ ID NO: 1.

Embodiment 15. A fusion protein comprising the modified polypeptide of any one of embodiments 1-14 and a heterologous polypeptide.

Embodiment 16. The fusion protein of embodiment 15, wherein the heterologous polypeptide is an Fc protein, a fluorescent protein, an enzyme, an antibody or antigen-binding protein, a cytokine, a cellular ligand or receptor, or serum albumin.

Embodiment 17. The fusion protein of embodiment 15 or embodiment 16, comprising the amino acid sequence of SEQ ID NO: 17.

Embodiment 18. A composition comprising the modified polypeptide of any one of embodiments 1-14, or the fusion protein of any one of embodiments 15-17, and a pharmaceutically acceptable carrier.

Embodiment 19. An in vitro method of inhibiting CMV replication, comprising contacting the CMV with the modified polypeptide of any one of embodiments 1-14, the fusion protein of any one of embodiments 15-17, or the composition of embodiment 18.

Embodiment 20. A method of inhibiting CMV replication and/or spread in a subject, comprising administering to the subject a therapeutically effective amount of the modified polypeptide of any one embodiments 1-14, the fusion protein of any one of embodiments 15-17, or the composition of embodiment 18, thereby inhibiting CMV replication and/or spread in the subject.

Embodiment 21. A method of treating or inhibiting CMV infection in a subject, comprising administering to the subject a therapeutically effective amount of the modified polypeptide of any one embodiments 1-14, the fusion protein of any one of embodiments 15-17, or the composition of embodiment 18, thereby treating or inhibiting CMV infection in the subject.

Embodiment 22. A nucleic acid molecule encoding the modified polypeptide of any one of embodiments 1-14 or the fusion protein of any one of embodiments 15-17.

Embodiment 23. A vector comprising the nucleic acid molecule of embodiment 22.

Embodiment 24. A composition comprising the nucleic acid molecule of embodiment 22 or the vector of embodiment 23, and a pharmaceutically acceptable carrier.

Embodiment 25. A method of inhibiting CMV replication and/or spread in a subject, comprising administering to the subject a therapeutically effective amount of the nucleic acid molecule of embodiment 22, the vector of embodiment 23, or the composition of embodiment 24, thereby inhibiting CMV replication and/or spread in the subject.

Embodiment 26. A method of treating or inhibiting CMV infection in a subject, comprising administering to the subject a therapeutically effective amount of the nucleic acid molecule of embodiment 22, the vector of embodiment 23, or the composition of embodiment 24, thereby treating or inhibiting CMV infection in the subject.

Embodiment 27. The method of any one of embodiments 19, 20, 25 and 26, wherein the subject is (i) a female subject who is pregnant; (ii) an infant whose mother is positive for CMV; (iii) a subject with an immunodeficiency; (iv) a transplant recipient; or (v) a subject who is immunosuppressed.

The following examples are provided to illustrate certain particular features and/or embodiments. These examples should not be construed to limit the disclosure to the particular features or embodiments described.

EXAMPLES

Example 1: A Deep Mutational Scan of PDGFRα D2-D3 Domains for Trimer Binding in the Presence of PDGFs The glycoprotein trimer from CMV strain TB40/E (BAC4 clone, Sinzger et al., *J Gen Virol.* 2008 February; 89(Pt 2):359-368) was expressed in Expi293F cells, a suspension derivative of human HEK 293. The transmembrane helix of gH was deleted to produce a soluble complex, and the gO subunit, which directly contacts PDGFRα (Kabanova et al., *Nat Microbiol.* 2016 Jun. 6; 1(8):16082; Wu et al., *PLoS*

Figure 7:
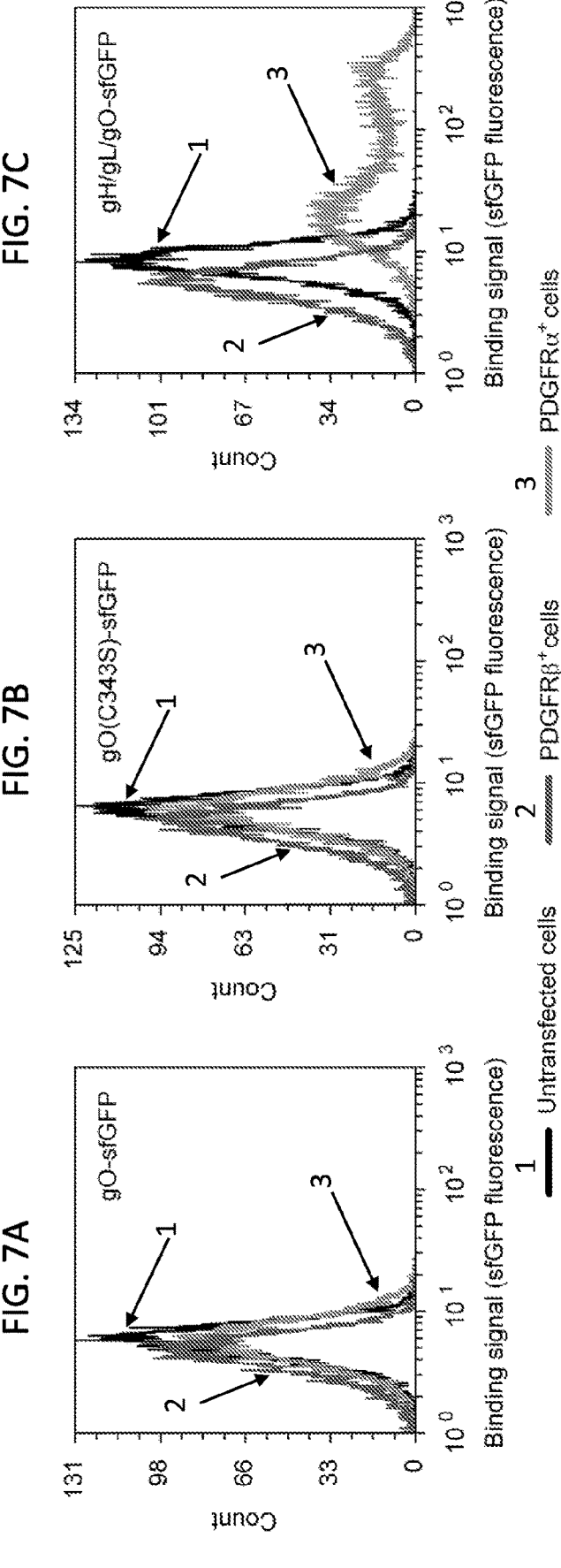
FIGS. 7A-7C: Binding of gO-sfGFP to PDGFRα-positive cells is dependent on co-expression of gH and gL. Expi293F cells were incubated with medium from cells expressing (FIG. 7A) gO-sfGFP, (FIG. 7B) gO(C343S)-sfGFP or (FIG. 7C) gH/gL/gO-sfGFP, washed and analyzed by flow cytometry. Cells were either untransfected, expressing PDGFRβ or expressing PDGFRα. High binding signal that was specific for PDGFRα-positive cells was only observed for medium containing all three components of the HCMV trimer.

*Pathog.* 2017 April; 13(4):e1006281; Stegmann et al., J Virol. 2019 Jun. 1; 93(11):93), was fused at its C-terminus to superfolder GFP (sfGFP; Pédelacq et al., *Nat Biotechnol.* 2006 January; 24(1):79-88) for fluorescence detection. Medium from gH/gL/gO-sfGFP expressing cells was incubated with Expi293F cells transfected with an episomal plasmid encoding PDGFRα. Trimer binding was proportional to PDGFRα surface expression (determined by flow cytometry using antibody staining of an extracellular c-myc epitope tag at the PDGFRα N-terminus; FIGS. 1A and 1B), and was inhibited by co-incubation with an equimolar mixture of PDGF-AA, AB, BB, and CC (FIG. 1D). Medium from cells expressing gO-sfGFP alone, either the wild-type sequence or carrying the mutation C351S (C343S based on numbering of gO from the TB40/E strain) to remove the exposed cysteine that would ordinarily form a disulfide to gL-C144 (Ciferri et al., *Proc Natl Acad Sci USA* 112: 1767-1772, 2015), failed to display high binding signal to PDGFRα positive cells (FIG. 7). The binding signal is therefore dependent on co-expression with gH and gL, suggesting that it is trimer as opposed to monomeric gO that engages the receptor.

A single site-saturation mutagenesis (SSM) library of PDGFRα was constructed encompassing all single amino acid mutations in the D2-D3 domains (a.a. D123-E311), and transfected into Expi293F cells under conditions that typically yield no more than one sequence variant per cell, providing a tight link between genotype and phenotype (Heredia et al., *J Immunol.* 2018 Apr. 20; 200(11): ji1800343-3839). When incubated with gH/gL/gO-sfGFP medium at subsaturating dilutions, cells expressing the SSM library were indistinguishable from cells expressing wild-type PDGFRα (FIGS. 1B and 1C). Typically, many mutations adversely impact protein activity through destabilization of folded structure or damage to functional sites, and loss-of-function variants tend to dominate naïve libraries prior to any selection. The finding that deleterious mutations were not prevalent in the naïve SSM library indicated that CMV trimer binding is resistant to most single non-synonymous mutations in the PDGFRα D2-D3 domains.

By comparison, many cells expressing the SSM library displayed higher trimer binding in the presence of PDGFs than cells expressing wild-type PDGFRα (FIGS. 1E and 1F). Thus, there appeared to be many PDGFRα mutations that selectively lost PDGF affinity. To identify these mutations, PDGFRα-expressing cells that had elevated CMV trimer binding in the presence of competing PDGFs were collected by fluorescence-activated cell sorting (FACS). This is referred to as the UL74-High sort (see green gate in FIG. 1F). Within the same experiment, cells expressing PDGFRα but displaying low trimer binding were also collected, referred to as the UL74-Low sort (see FIG. 1F). PDGFRα mutants that lose affinity for trimer, or have enhanced affinity for competing PDGFs, were preferentially enriched in the UL74-Low sort. PDGFRα mutants that fail to express were depleted from both sorted populations. Following Illumina sequencing of the naïve plasmid library and transcripts from the sorted populations, the enrichment ratios for all 3,780 substitutions in the D2-D3 domains were calculated to define a local mutational landscape (FIG. 2A). Data from independent replicates are highly correlated (FIGS. 2B-2G), indicating the data are accurate.

Figure 8:
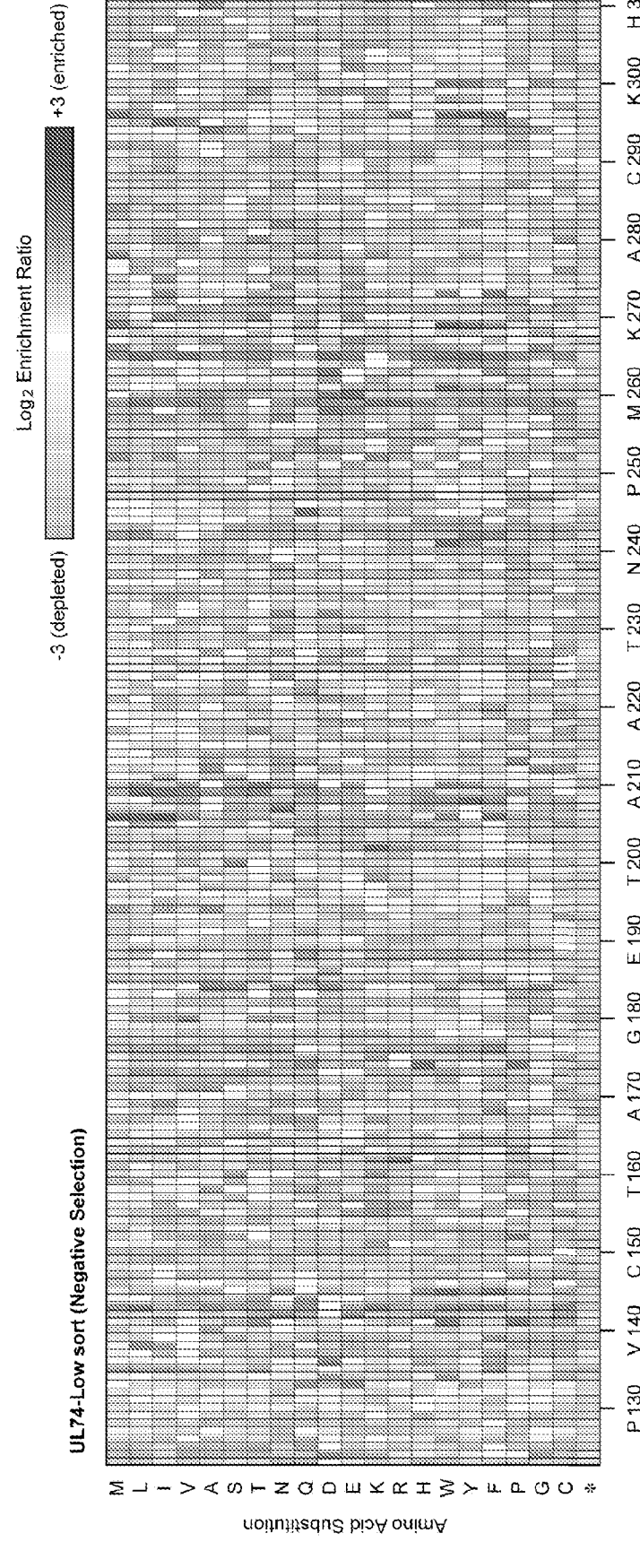
FIG. 8: No hot spots for enriched mutations in the negative selection for loss of HCMV trimer binding. $\log_2$ enrichment ratios for single amino acid substitutions of PDGFRα are plotted based on their enrichment in the UL74-Low sort, from −3 (depleted) to +3 (enriched). Amino acid position is on the horizontal axis, and substitutions are on the vertical axis. *, stop codon. Mutations to critical residues for HCMV trimer binding are expected to be enriched in this negative selection. Compare to the positive selection shown in FIG. 2A, which uses the same scale.

Example 2: PDGF Interactions are Uniquely Sensitive to Mutational Disruption of Folded Structure in the D2-D3 Domains Enrichment ratios for nonsynonymous mutations are anti-correlated between the UL74-High and UL74-Low sorts, with few mutations other than premature stop codons being depleted in both selections. Hence, substitution mutations in PDGFRα D2-D3 domains suffer little cost to surface localization, even though many mutations will almost certainly destabilize the domain fold. This differs markedly from a prior mutational scan of a multidomain membrane protein expressed in human cells, where nonconservative mutations buried within folded structure prevented protein trafficking to the plasma membrane due to intracellular retention by quality control machinery (Park et al., *J Biol Chem.* 2019; 294(13):4759-4774). When mapping experimental conservation scores to the structure of PDGF-bound PDGFRα (modeled from the crystal structure of PDGF-BB-bound PDGFRβ; PDB ID 3MJG; Shim et al., *Proc Natl Acad Sci USA.* 2010 Jun. 22; 107(25):11307-11312), enriched mutations are found to cluster to buried core positions and the PDGF interface (FIGS. 3A-3E). These include substitutions that create cavities, steric clashes, and/or introduce buried ionizable groups; these mutations are incompatible with biophysical principles governing protein folding and will destabilize folded structure. PDGFRα mutants with disrupted structure have therefore preferentially lost affinity to PDGFs, thereby reducing competition and enhancing binding of the CMV trimer. The epitope bound by the HCMV trimer is ambiguous from the data (FIG. 8), but must be at least partially independent of proper D2-D3 conformation, although partial structure may remain. This is consistent with either key contacts to the HCMV trimer residing on linear PDGFRα segments and loops, similar to how many antibodies recognize conformation-independent epitopes, or with favorable interactions to the HCMV trimer being distributed over a broad surface (possibly even beyond the D2-D3 domains) such that localized disruptions are tolerated. Libraries encompassing double or higher order PDGFRα, mutations may further resolve details of the binding mechanism.

Table 1 provides a list of PDGFRα mutations that exhibited reduced competition from PDGF for binding to CMV.

TABLE 1

| | | PDGFRα mutants with reduced competition from PDGF for binding to CMV | | | |
| --- | --- | --- | --- | --- | --- |
| V126P | R151A | C189M | L214S | N239I | L261K * |
| F128A | R151P | C189L | L214N | N239V | L261R * |
| F128D | R151C | C189I | L214Q | N239A | L261P * |
| F128E | T153C | C189V | L214R | N239S | L261C * |
| K128K | D154T | C189A | L214H | N239T | E262P |
| F128P | P155C | C189S | L214Y | N239P | K270P |
| D135M | E156P | C189T | L214P | N240D | L271V * |
| D135L | T157E | C189N | L214C | N240E | L271A * |
| D135I | T157C | C189Q | L216D | N240K | L271S * |
| D135V | V159D | C189D | L216E | N240R | L271T * |
| L137A * | V159E | C189E | L216K | N240W | L271N * |
| L137S * | V159W | C189K | L216R | N240Y | L271Q * |
| L137T * | V159G | C189R | L216G | N240F | L271D * |
| L137N * | V159C | C189H | L216C | N240P | L271E * |
| L137Q * | T160P | C189W | E217P | E241G | L271A * |
| L137D * | L161A | C189P | M218D | V242A * | L271R * |
| L137E * | L161T | C189G | M218K | V242S * | L271H * |
| L137K * | L161Q | A191P | M218R | V242T * | L271W* |
| L137R * | L161D | G195P | M218P | V242N * | L271Y * |
| L137G * | L161E | F203D | V224G | V242Q * | L271F* |
| L137C * | L161R | F203E | Y225S | V242D * | L271P* |
| V138D | L161W | F203K | Y225E | V242E * | L271G * |
| V138E | L161G | F203R | Y225K | V242K * | L271C * |
| V138H | L161C | F203P | Y225R | V242R * | V272P |
| V138P | N163P | F203G | Y225P | V242P * | Y273E |
| V138G | Y172M | V205Q | Y225G | V242G * | Y273K |
| V138C | Y172V | V205R | K226D | V242C * | Y273R |
| I139E * | Y172D | V205H | K226W | V243S | L275T |

TABLE 1-continued

| | | PDGFRα mutants with reduced competition from PDGF for binding to CMV | | | |
| --- | --- | --- | --- | --- | --- |
| I147C | Y172E | V205C | K226P | V243T | V277T |
| I148R | R175C | Y206S * | E229T | V243N | C290L |
| I148H | G177T | Y206T * | I231A | V243Q | C290V |
| C150M | G177Q | Y206Q * | I231K | V243D | C290A |
| C150L | G177K | Y206D * | I231C | V243E | A292M |
| C150I | G177R | Y206E * | V233K | V243K | A292K |
| C150V | G177P | Y206K * | C235A | V243R | A292R |
| C150A | F178D | Y206R * | C235D | V243W | A292H |
| C150S | F178R | Y206P * | A236P | V243Y | A292Y |
| C150T | F178P | Y206G * | V237N | V243F | A292F |
| C150N | G180P | Y206C * | V237Q | V243P | Q294W |
| C150Q | F182A | L208N * | V237D | V243G | Q294Y |
| C150D | F182T | L208Q * | V237E | V243C | K303P |
| C150E | F182P | L208D * | V237K | D244P | I307Q |
| C150K | G185K * | L208E * | V237R | L245K | |
| C150R | G185R * | L208K * | V237H | L245R | |
| C150H | Y187T | L208R * | V237W | L245P | |
| C150W | Y187K | L208C * | V237Y | Q246P | |
| C150Y | Y187R | | V237F | W247P | |
| C150F | I188P | | V237P | W247G | |
| C150P | | | F238P | | |
| C150G | | | | | |

* Mutations residing at the PDGFRα-PDGF interface. Other mutations most likely have indirect structural effects. Amino acid numbering is with respect to SEQ ID NO: 1.

Example 3: Surface Mutations at the PDGF Binding Site Favor PDGFRα Specificity Towards the CMV Trimer The PDGFRα mutational landscape for high trimer binding in the presence of competing PDGF reveals key surface residues as hot spots for enriched mutations, especially PDGFRα residues L137, L208 and V242 that contact the protruding PDGF subunit, and Y206 which packs between the protruding and receding PDGF subunits (FIGS. 3D and 3E; residue numbers are based on SEQ ID NO: 1). Mutations to these residues will disrupt the PDGFRα-PDGF interface, especially by the addition of polar substitutions that invert the chemical properties of the highly hydrophobic binding site. CMV trimer interactions are persisting in these PDGFRα mutants. Overall, enrichment of mutations for increased HCMV trimer binding in the presence of competing PDGFs is highly correlated to the mutated residue's connectivity within the D2-D3 core or across the PDGFRα-PDGF interface (FIG. 9), emphasizing the selective importance of PDGFRα conformation and surface contacts in the D2-D3 cleft for high affinity PDGF interactions.

Figures 4A, 4B, 4C:
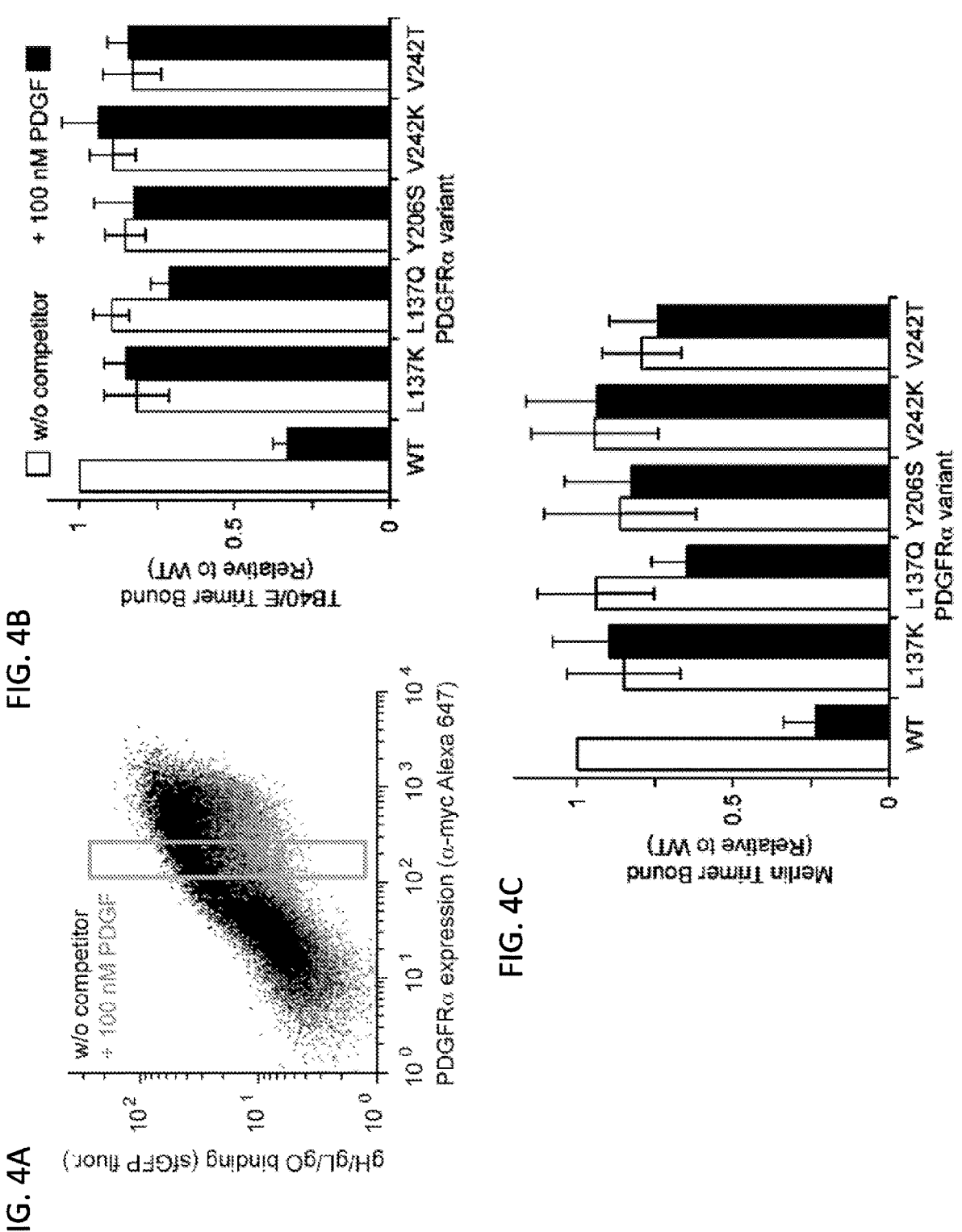
FIGS. 4A-4C: Validation of selected mutants in PDGFRα that block PDGF competition.

Five mutations on the PDGFRα surface (L137K, L137Q and Y206S in D2, and V242K and V242T in D3, with respect to SEQ ID NO: 1) were validated as having desirable binding properties by targeted mutagenesis. As predicted from the deep mutational scan, these PDGFRα variants maintain wild-type levels of binding to CMV trimer from the TB40/E strain, yet have diminished sensitivity to the addition of competing PDGFs, demonstrating successful engineering of specificity towards the viral target (FIGS. 4A and 4B). Since the mechanism of trimer binding to receptor has not been resolved at atomic or even residue-level resolution, it remains uncertain whether the viral genome could mutate to distinguish wild-type from engineered PDGFRα. This concern is partially alleviated by the observation that the engineered PDGFRα mutants maintain high binding to the CMV trimer from the Merlin clinical strain (Stanton et al., *J Clin Invest.* 2010 September; 120(9):3191-3208) (FIG. 4C), which has relatively high natural sequence variation compared to TB40/E (79% identity between glycoproteins O; compare SEQ ID NO: 3 and SEQ ID NO: 6), especially in the N-terminus of glycoprotein O where important interactions to PDGFRα reside (Stegmann et al., *J Virol.* 2019 Jun. 1; 93(11):93).

Figures 9, 10A, 10B, 10C:
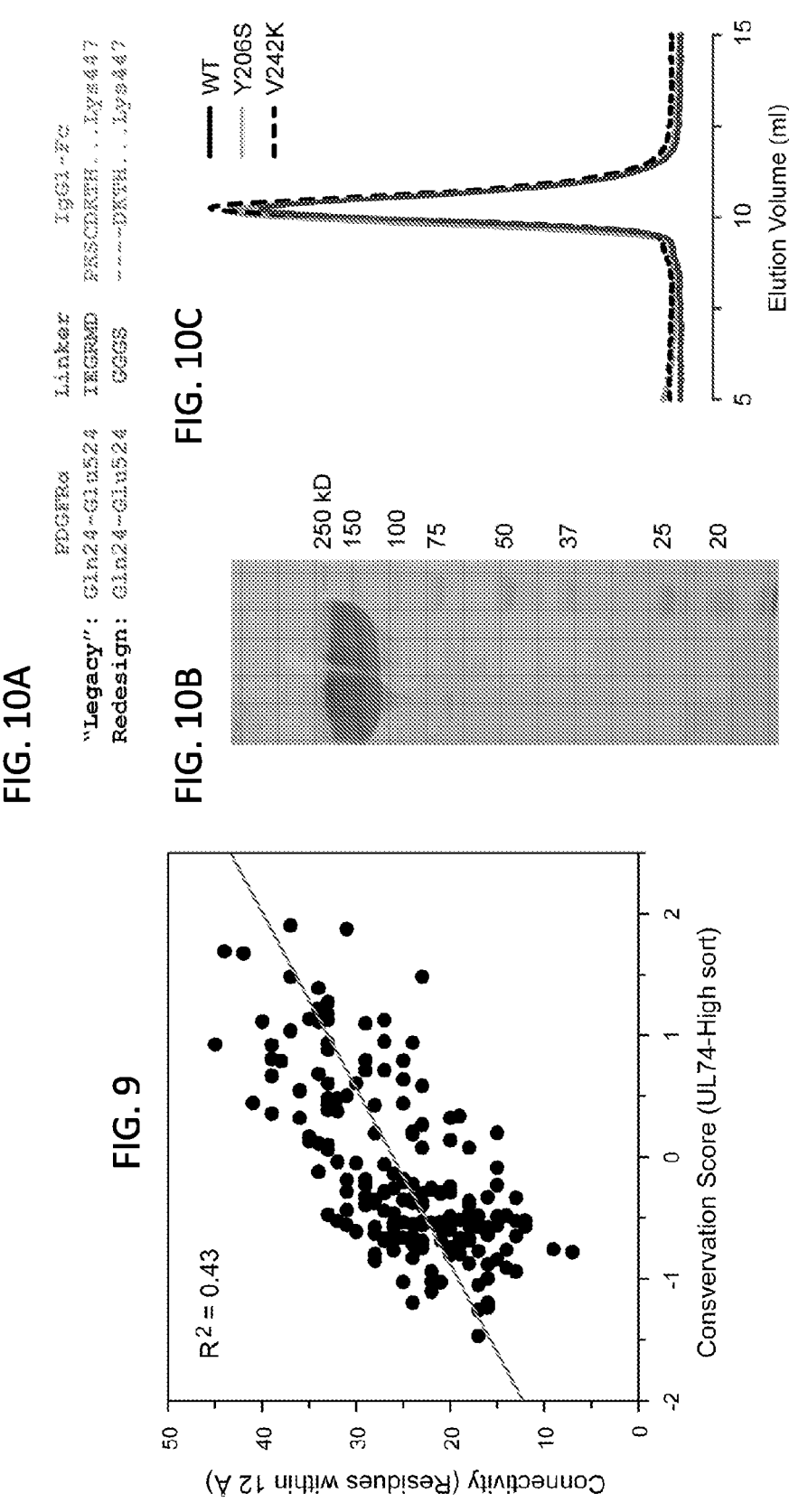
FIG. 9: PDGFRα mutations that increase HCMV trimer binding in the presence of competing PDGFs are biased to structurally connected residues. Residue conservation scores in the UL74-High deep mutational scan were calculated by averaging the $\log_2$ enrichment ratios for all 20 possible amino acids at each diversified position. PDGFRα residues where mutations tend to increase HCMV trimer binding in the presence of competing PDGFs have higher positive scores. A residue's conservation score is correlated with its connectivity in the modeled PDGF-bound PDGFRα structure, where connectivity is quantified by the number of neighboring residues within a 12 Å radius. Highly connected residues are either buried in the hydrophobic cores of the D2-D3 domains, or are buried at the PDGF binding interface.
FIGS. 10A-10C: Purification of soluble IgG1 Fc-fused PDGFRα.

Fusion of soluble proteins to immunoglobulin Fc confers multiple desirable properties for a therapeutic (Czajkowsky et al., *EMBO Mol Med* 4: 1015-1028, 2012). Multimerized Fc chains impose avidity for enhanced apparent affinity, and Fc moieties are engaged by multiple receptors to enhance serum half-life or evoke effector functions, including complement activation and antibody-dependent cell-mediated cytotoxicity (Czajkowsky et al., *EMBO Mol Med* 4: 1015-1028, 2012). Soluble PDGFRα fused to the Fc region of human IgG1 was shown to bind HCMV trimer when first identified as its receptor (Kabanova et al., *Nat Microbiol* 1: 16082, 2016), and the neutralization properties of Fc-fused soluble PDGFRα (sPDGFRα-Fc) have been explored since in greater detail (Wu et al., *PLoS Pathog* 13: e1006281, 2017). These prior studies used commercially supplied sPDGFRα-Fc featuring a random linker of mixed amino acids that connects to the upper hinge of IgG1, upstream of Cys-220 that would ordinarily form a disulfide to the antibody light chain (FIG. 10A). The nature of this Fc fusion may cause manufacturing liabilities if Cys-220 is exposed and free (this construct is referred to herein as "legacy" sPDGFRα-Fc).

An alternative sPDGFRα-Fc construct was designed that includes the PDGFRα signal peptide (a.a. 1-23 of SEQ ID NO: 1), ectodomain (a.a. 24-524 of SEQ ID NO: 1), a GGGS linker (SEQ ID NO: 10), and human IgG1 Fc beginning at Asp-221 (see SEQ ID NO: 11 and FIG. 10A), yielding the following amino acid sequence:

```
                                        (SEQ ID NO: 17)
MGTSHPAFLVLGCLLTGLSLILCQLSLPSILPNENEKVVQLNSSFSLRCF

GESEVSWQYPMSEEESSDVEIRNEENNSGLFVTVLEVSSASAAHTGLYTC

YYNHTQTEENELEGRHIYIYVPDPDVAFVPLGMTDYLVIVEDDDSAIIPC

RTTDPETPVTLHNSEGVVPASYDSRQGFNGTFTVGPYICEATVKGKKFQT

IPFNVYALKATSELDLEMEALKTVYKSGETIVVTCAVFNNEVVDLQWTYP

GEVKGKGITMLEEIKVPSIKLVYTLTVPEATVKDSGDYECAARQATREVK

EMKKVTISVHEKGFIEIKPTFSQLEAVNLHEVKHFVVEVRAYPPPRISWL

KNNLTLIENLTEITTDVEKIQEIRYRSKLKLIRAKEEDSGHYTIVAQNED

AVKSYTFELLTQVPSSILDLVDDHHGSTGGQTVRCTAEGTPLPDIEWMIC

KDIKKCNNETSWTILANNVSNIITEIHSRDRSTVEGRVTFAKVEETIAVR

CLAKNLLGAENRELKLVAPTLRSEGGGSDKTHTCPPCPAPELLGGPSVFL

FPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKSLS

LSPGK
```

Both sPDGFRα-Fc constructs bind membrane-localized HCMV trimer with equal affinity, and subsequent studies focused exclusively on the redesigned fusion protein.

Figure 11B:
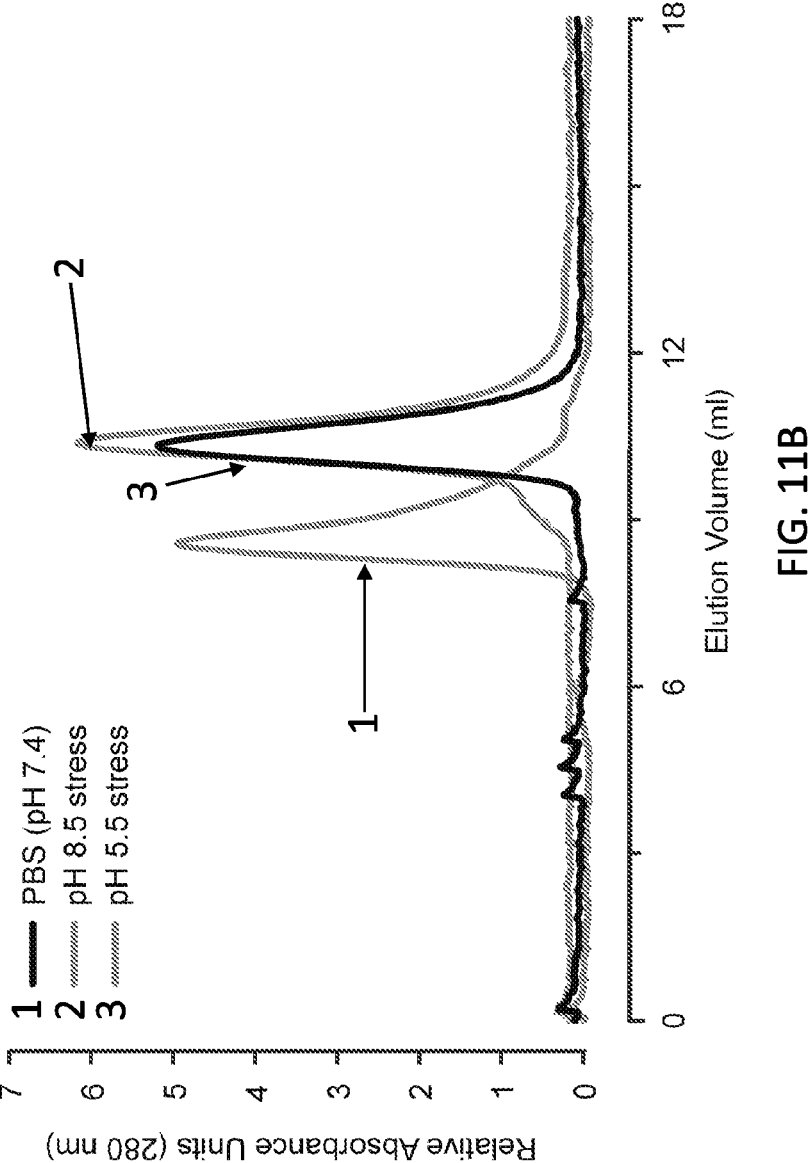
FIGS. 11A-11B: Chemical stress tests of sPDGFRα-Fc.
Figure 11A:
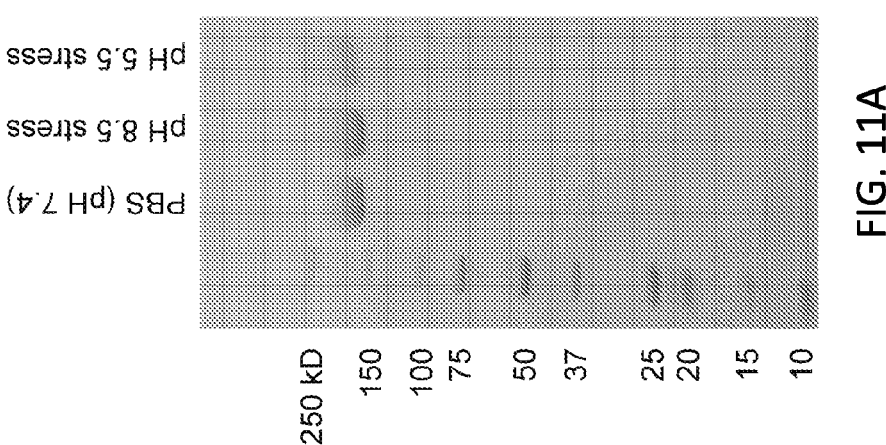

Soluble PDGFRα-Fc was expressed in Expi293F culture, and was isolated by affinity capture and size exclusion chromatography (SEC) to very high purity (FIGS. 10B and 10C). The purified protein was monodisperse by SEC, and the final yield was high (>25 mg/L of transfected culture without any optimization). Soluble PDGFRα-Fc V242K was stressed for 7 days at 40° C., pH 8.5, to promote asparagine deamidation and protein denaturation (Lu et al., *MAbs* 11: 45-57, 2019), yet remained mostly stable based on the SEC profile (FIG. 11). A harsher stress for 14 days at 40° C., pH 5.5, to promote asparagine isomerization and protein denaturation (Lu et al., *MAbs* 11: 45-57, 2019) caused sPDGFRα-Fc V242K to form soluble aggregates (FIG. 11). It was concluded that the protein has moderate stability and is suitable for further manufacturing development.

Two PDGFRα mutations, Y206S and V242K, were explored as Fc-fused soluble orthogonal receptors. Binding of the soluble receptors was measured towards HCMV trimer expressed at the cell surface, with gL and gO subunits tagged at their C-termini with short peptide epitopes, and gH expressed as full-length protein with its native transmembrane domain. The Y206S mutant had reduced binding to HCMV trimer compared to wild-type receptor, but sPDGFRα-Fc V242K bound HCMV trimer from Merlin and TB40/E strains with equal low nanomolar affinity. Aspects of these experiments were replicated with independent protein preparations (FIG. 12A). Furthermore, fusions of wild-type and V242K sPDGFRα with the Fc region of IgG3 also bound similarly to trimer from the TB40/E and Merlin strains (FIGS. 12B and 12C). Compared to IgG1, IgG3 has lower affinity for the neonatal Fc receptor (FcRn), which is associated with reduced serum half-life and placental transfer (Vidarsson et al., *Front Immunol* 5: 520, 2014; Roopenian et al., *J Immunol* 170: 3528-3533, 2003). It was speculated that these features may be advantageous in the treatment of pregnant women during acute HCMV infection to achieve a lower dose in the developing fetus, thereby further addressing safety concerns.

Figures 5A, 5B:
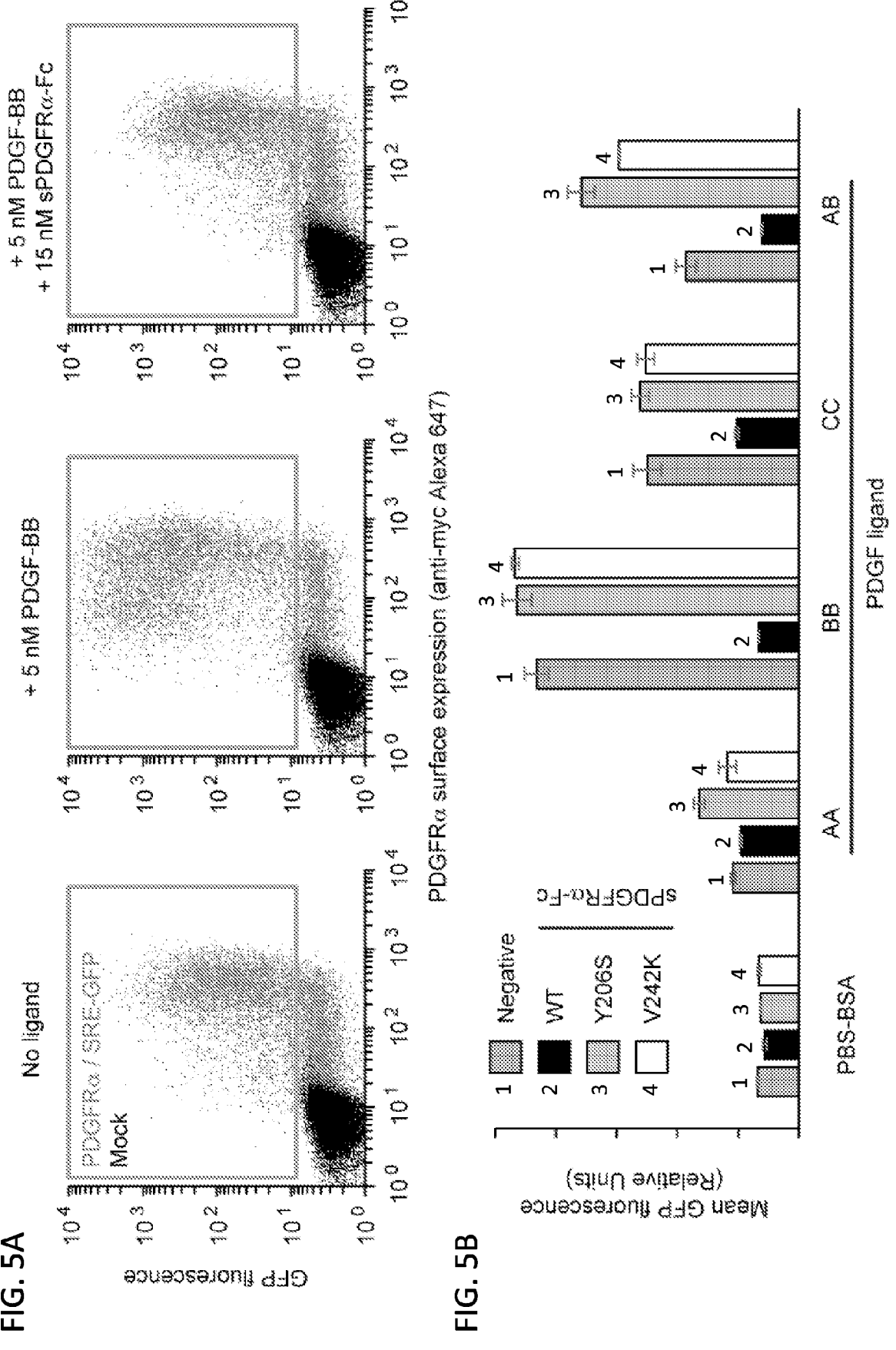
FIGS. 5A-5B: Soluble PDGFRα variants that no longer inhibit PDGF signaling.

To further validate that the engineered receptors have lost growth factor interactions, their ability to inhibit PDGF signaling was assessed. Expi293F cells were transfected with a reporter plasmid encoding wild-type PDGFRα and a destabilized fluorescent protein (EGFP-PEST) (Li et al., *J Biol Chem* 273: 34970-34975, 1998) under the control of a serum response element (SRE) (Reichhart et al., *Angew Chem Int Ed Engl* 55: 6339-6342, 2016). Treatment with PDGFs upregulates EGFP-PEST expression, which is inhibited by wild-type sPDGFRα-Fc acting as a decoy receptor (FIG. 5). As intended, both sPDGFRα-Fc Y206S and V242K failed to inhibit PDGF signaling (FIG. 5B). However, the engineered receptors, in particular sPDGFRα-Fc Y206S, enhanced the response to PDGF-A ligands, which may be due to a generic 'carrier protein' effect (PDGF ligands and their receptors are highly hydrophobic (Shim et al., *Proc Natl* Acad Sci USA 107: 11307-11312, 2010) and are generally formulated with a carrier such as serum albumin), and non-specific gamma globulin has no such effect (FIG. 13).

Human PDGFRα coding sequence (SEQ ID NO: 2) and its translation (SEQ ID NO: 1). Numbers correspond to amino acid residues. Residues at the PDGFRα-PDGF interface that were mutated and found to preferentially retain CMV trimer binding are in bold and underlined.

```
atg ggg act tcc cat ccg gcg ttc ctg gtc tta ggc tgt ctt ctc aca ggg ctg agc cta
 M   G   T   S   H   P   A   F   L   V   L   G   C   L   T   G   L   S   L        20 atc ctc tgc cag ctt tca tta ccc tct atc ctt cca aat gaa aat gaa aag gtt gtg cag
 I   L   C   Q   L   S   L   P   S   I   L   P   N   E   N   E   K   V   Q        40 ctg aat tca tcc ttt tct ctg aga tgc ttt ggg gag agt gaa gtg agc tgg cag tac ccc
 L   N   S   S   F   S   L   R   C   F   G   E   S   E   V   S   W   Q   Y   P    60 atg tct gaa gaa gag agc tcc gat gtg gaa atc aga aat gaa gaa aac aac agc ggc ctt
 M   S   E   E   E   S   S   D   V   E   I   R   N   E   E   N   N   S   G   L    80 ttt gtg acg gtc ttg gaa gtg agc agt gcc tcg gcg gcc cac aca ggg ttg tac act tgc
 F   V   T   V   L   E   V   S   S   A   S   A   A   H   T   G   L   Y   T   C   100 tat tac aac cac act cag aca gaa gag aat gag ctt gaa ggc agg cac att tac atc tat
 Y   Y   N   H   T   Q   T   E   E   N   E   L   E   G   R   H   I   Y   I   Y   120 gtg cca gac cca gat gta gcc ttt gta cct cta gga atg acg gat tat tta gtc atc gtg
 V   P   D   P   D   V   A   F   V   P   L   G   M   T   D   Y   L   V   I   V   140 gag gat gat gat tct gcc att ata cct tgt cgc aca act gat ccc gag act cct gta acc
 E   D   D   D   S   A   I   I   P   C   R   T   T   D   P   E   T   P   V   T   160 tta cac aac agt gag ggg gtg gta cct gcc tcc tac gac agc aga cag ggc ttt aat ggg
 L   H   N   S   E   G   V   V   P   A   S   Y   D   S   R   Q   G   F   N   G   180 acc ttc act gta ggg ccc tat atc tgt gag gcc acc gtc aaa gga aag aag ttc cag acc
 T   F   T   V   G   P   Y   I   C   E   A   T   V   K   G   K   K   F   Q   T   200 atc cca ttt aat gtt tat gct tta aaa gca aca tca gag ctg gat cta gaa atg gaa gct
 I   P   F   N   V   Y   A   L   K   A   T   S   E   L   D   L   E   M   E   A   220 ctt aaa acc gtg tat aag tca ggg gaa acg att gtg gtc acc tgt gct gtt ttt aac aat
 L   K   T   V   Y   K   S   G   E   T   I   V   V   T   C   A   V   F   N   N   240 gag gtg gtt gac ctt caa tgg act tac cct gga gaa gtg aaa ggc aaa ggc atc aca atg
 E   V   V   D   L   Q   W   T   Y   P   G   E   V   K   G   K   G   I   T   M   260 ctg gaa gaa atc aaa gtc cca tcc atc aaa ttg gtg tac act ttg acg gtc ccc gag gcc
 L   E   E   I   K   V   P   S   I   K   L   V   Y   T   L   T   V   P   E   A   280 acg gtg aaa gac agt gga gat tac gaa tgt gct gcc cgc cag gct acc agg gag gtc aaa
 T   V   K   D   S   G   D   Y   E   C   A   A   R   Q   A   T   R   E   V   K   300 gaa atg aag aaa gtc act att tct gtc cat gag aaa ggt ttc att gaa atc aaa ccc acc
 E   M   K   K   V   T   I   S   V   H   E   K   G   F   I   E   I   K   P   T   320 ttc agc cag ttg gaa gct gtc aac ctg cat gaa gtc aaa cat ttt gtt gta gag gtg cgg
 F   S   Q   L   E   A   V   N   L   H   E   V   K   H   F   V   V   E   V   R   340 gcc tac cca cct ccc agg ata tcc tgg ctg aaa aac aat ctg act ctg att gaa aat ctc
 A   Y   P   P   P   R   I   S   W   L   K   N   N   L   T   L   I   E   N   L   360 act gag atc acc act gat gtg gaa aag att cag gaa ata agg tat cga agc aaa tta aag
 T   E   I   T   T   D   V   E   K   I   Q   E   I   R   Y   R   S   K   L   K   380 ctg atc cgt gct aag gaa gaa gac agt ggc cat tat act att gta gct caa aat gaa gat
 L   I   R   A   K   E   E   D   S   G   H   Y   T   I   V   A   Q   N   E   D   400 gct gtg aag agc tat act ttt gaa ctg tta act caa gtt cct tca tcc att ctg gac ttg
 A   V   K   S   Y   T   F   E   L   L   T   Q   V   P   S   S   I   L   D   L   420 gtc gat gat cac cat ggc tca act ggg gga cag acg gtg agg tgc aca gct gaa ggc acg
 V   D   D   H   H   G   S   T   G   G   Q   T   V   R   C   T   A   E   G   T   440 ccg ctt cct gat att gag tgg atg ata tgc aaa gat att aag aaa tgt aat aat gaa act
 P   L   P   D   I   E   W   M   I   C   K   D   I   K   K   C   N   N   E   T   460 tcc tgg act att ttg gcc aac aat gtc tca aac atc atc acg gag atc cac tcc cga gac
 S   W   T   I   L   A   N   N   V   S   N   I   I   T   E   I   H   S   R   D   480 agg agt acc gtg gag ggc cgt gtg act ttc gcc aaa gtg gag gag acc atc gcc gtg cga
 R   S   T   V   E   G   R   V   T   F   A   K   V   E   E   T   I   A   V   R   500 tgc ctg gct aag aat ctc ctt gga gct gag aac cga gag ctg aag ctg gtg gct ccc acc
 C   L   A   K   N   L   L   G   A   E   N   R   E   L   K   L   V   A   P   T   520 ctg cgt tct gaa ctc acg gtg gct gct gca gtc ctg gtg ctg ttg gtg att gtg atc atc
 L   R   S   E   L   T   V   A   A   A   V   L   V   L   L   V   I   V   I   I   540
```

-continued

```
tca ctt att gtc ctg gtt gtc att tgg aaa cag aaa ccg agg tat gaa att cgc tgg agg
 S   L   I   V   L   V   V   I   W   K   Q   K   P   R   Y   E   I   R   W   R    560 gtc att gaa tca atc agc cca gat gga cat gaa tat att tat gtg gac ccg atg cag ctg
 V   I   E   S   I   S   P   D   G   H   E   Y   I   Y   V   D   P   M   Q   L    580 cct tat gac tca aga tgg gag ttt cca aga gat gga cta gtg ctt ggt cgg gtc ttg ggg
 P   Y   D   S   R   W   E   F   P   R   D   G   L   V   L   G   R   V   L   G    600 tct gga gcg ttt ggg aag gtg gtt gaa gga aca gcc tat gga tta agc cgg tcc caa cct
 S   G   A   F   G   K   V   V   E   G   T   A   Y   G   L   S   R   S   Q   P    620 gtc atg aaa gtt gca gtg aag atg cta aaa ccc acg gcc aga tcc agt gaa aaa caa gct
 V   M   K   V   A   V   K   M   L   K   P   T   A   R   S   S   E   K   Q   A    640 ctc atg tct gaa ctg aag ata atg act cac ctg ggg cca cat ttg aac att gta aac ttg
 L   M   S   E   L   K   I   M   T   H   L   G   P   H   L   N   I   V   N   L    660 ctg gga gcc tgc acc aag tca ggc ccc att tac atc atc aca gag tat tgc ttc tat gga
 L   G   A   C   T   K   S   G   P   I   Y   I   I   T   E   Y   C   F   Y   G    680 gat ttg gtc aac tat ttg cat aag aat agg gat agc ttc ctg agc cac cac cca gag aag
 D   L   V   N   Y   L   H   K   N   R   D   S   F   L   S   H   H   P   E   K    700 cca aag aaa gag ctg gat atc ttt gga ttg aac cct gct gat gaa agc aca cgg agc tat
 P   K   K   E   L   D   I   F   G   L   N   P   A   D   E   S   T   R   S   Y    720 gtt att tta tct ttt gaa aac aat ggt gac tac atg gac atg aag cag gct gat act aca
 V   I   L   S   F   E   N   N   G   D   Y   M   D   M   K   Q   A   D   T   T    740 cag tat gtc ccc atg cta gaa agg aaa gag gtt tct aaa tat tcc gac atc cag aga tca
 Q   Y   V   P   M   L   E   R   K   E   V   S   K   Y   S   D   I   Q   R   S    760 ctc tat gat cgt cca gcc tca tat aag aag aaa tct atg tta gac tca gaa gtc aaa aac
 L   Y   D   R   P   A   S   Y   K   K   K   S   M   L   D   S   E   V   K   N    780 ctc ctt tca gat gat aac tca gaa ggc ctt act tta ttg gat ttg ttg agc ttc acc tat
 L   L   S   D   D   N   S   E   G   L   T   L   L   D   L   L   S   F   T   Y    800 caa gtt gcc cga gga atg gag ttt ttg gct tca aaa aat tgt gtc cac cgt gat ctg gct
 Q   V   A   R   G   M   E   F   L   A   S   K   N   C   V   H   R   D   L   A    820 gct cgc aac gtc ctc ctg gca caa gga aaa att gtg aag atc tgt gac ttt ggc ctg gcc
 A   R   N   V   L   L   A   Q   G   K   I   V   K   I   C   D   F   G   L   A    840 aga gac atc atg cat gat tcg aac tat gtg tcg aaa ggc agt acc ttt ctg ccc gtg aag
 R   D   I   M   H   D   S   N   Y   V   S   K   G   S   T   F   L   P   V   K    860 tgg atg gct cct gag agc atc ttt gac aac ctc tac acc aca ctg agt gat gtc tgg tct
 W   M   A   P   E   S   I   F   D   N   L   Y   T   T   L   S   D   V   W   S    880 tat ggc att ctg ctc tgg gag atc ttt tcc ctt ggt ggc acc cct tac ccc ggc atg atg
 Y   G   I   L   L   W   E   I   F   S   L   G   G   T   P   Y   P   G   M   M    900 gtg gat tct act ttc tac aat aag atc aag agt ggg tac cgg atg gcc aag cct gac cac
 V   D   S   T   F   Y   N   K   I   K   S   G   Y   R   M   A   K   P   D   H    920 gct acc agt gaa gtc tac gag atc atg gtg aaa tgc tgg aac agt gag ccg gag aag aga
 A   T   S   E   V   Y   E   I   M   V   K   C   W   N   S   E   P   E   K   R    940 ccc tcc ttt tac cac ctg agt gag att gtg gag aat ctg ctg cct gga caa tat aaa aag
 P   S   F   Y   H   L   S   E   I   V   E   N   L   L   P   G   Q   Y   K   K    960 agt tat gaa aaa att cac ctg gac ttc ctg aag agt gac cat cct gct gtg gca cgc atg
 S   Y   E   K   I   H   L   D   F   L   K   S   D   H   P   A   V   A   R   M    980 cgt gtg gac tca gac aat gca tac att ggt gtc acc tac aaa aac gag gaa gac aag ctg
 R   V   D   S   D   N   A   Y   I   G   V   T   Y   K   N   E   E   D   K   L   1000 aag gac tgg gag ggt ggt ctg gat gag cag aga ctg agc gct gac agt ggc tac atc att
 K   D   W   E   G   G   L   D   E   Q   R   L   S   A   D   S   G   Y   I   I   1020 cct ctg cct gac att gac cct gtc cct gag gag gag gac ctg ggc aag agg aac aga cac
 P   L   P   D   I   D   P   V   P   E   E   E   D   L   G   K   R   N   R   H   1040 agc tcg cag acc tct gaa gag agt gcc att gag acg ggt tcc agc agt tcc acc ttc atc
 S   S   Q   T   S   E   E   S   A   I   E   T   G   S   S   S   S   T   F   I   1060
```

-continued

```
aag aga gag gac gag acc att gaa gac atc gac atg atg gat gac atc ggc ata gac tct
 K   R   E   D   E   T   I   E   D   I   D   M   M   D   D   I   G   I   D   S  1080 tca gac ctg gtg gaa gac agc ttc ctg taa
 S   D   L   V   E   D   S   F   L   -                                        1089
```

Example 4: Orthogonal PDGFRα-Based Receptors Targeting HCMV Trimer Potently Neutralize Virus The two representative orthogonal receptors, PDGFRα Y206S and V242K, were evaluated for their efficacy to neutralize virus infection. HCMV trimer-only lab strain AD169 (Wang and Shenk, *J Virol* 79: 10330-10338, 2005; Yu et al, *J Virol* 76: 2316-2328, 2002) and trimer/pentamer-expressing clinical strain TB40/E (Sinzger et al., *J Gen Virol* 89: 359-368, 2008) were grown on PDGFRα-positive MRC-5 fibroblasts and PDGFRα-negative ARPE-19 epithelial cells. Three cell lines were infected by both HCMV strains: MRC-5, ARPE-19, and ARPE-19RA, which are stably transfected with PDGFRα to confer susceptibility to AD169 (Wu et al., *Proc Natl Acad Sci USA* 115: E9889—E9898, 2018).

Figure 6:
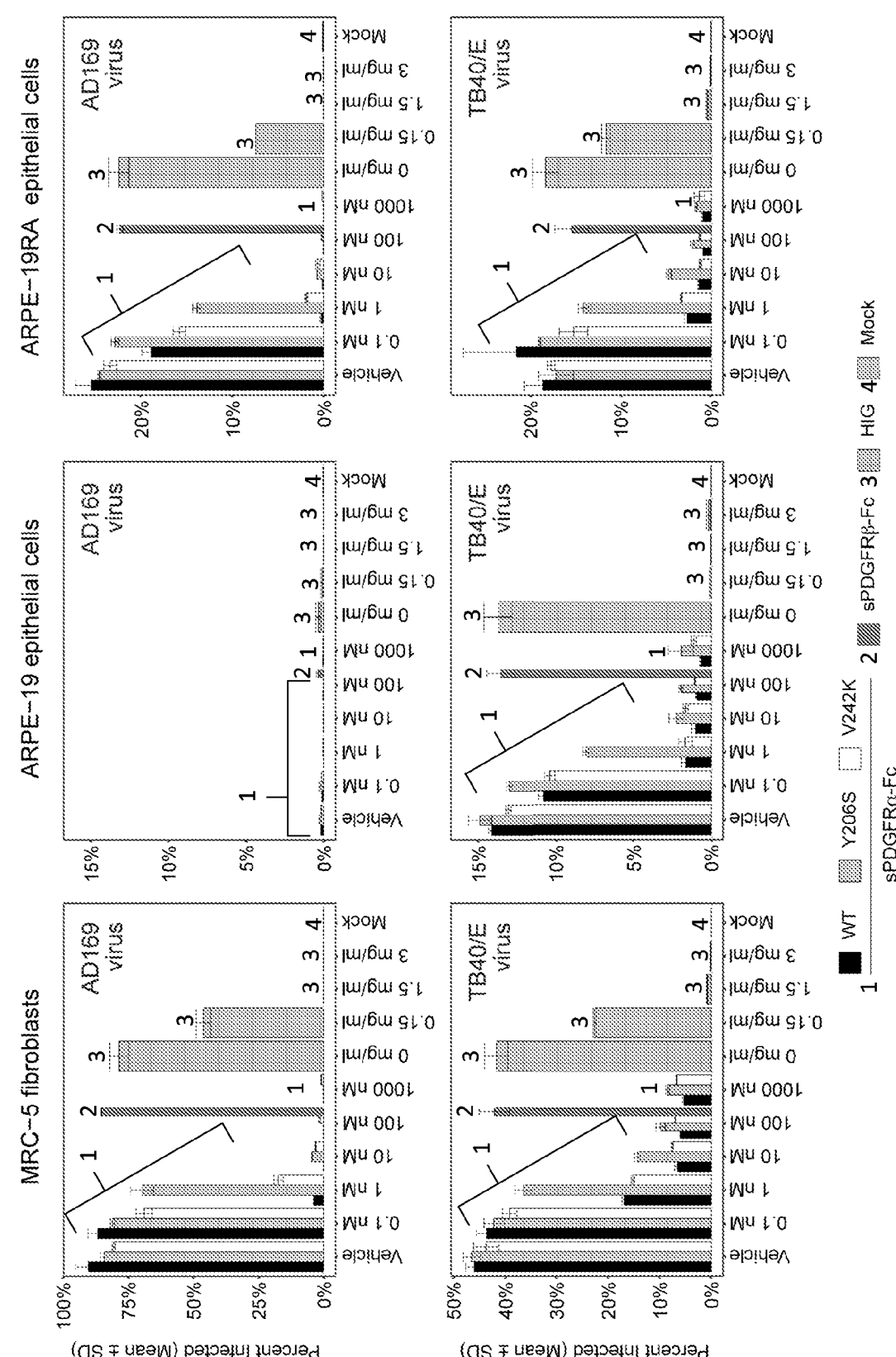
FIG. 6: Soluble orthogonal receptors for HCMV trimer neutralize virus. MRC-5 (left), ARPE-19 (middle) and ARPE-19RA (right) cells were infected with HCMV strains AD169 (grown in MRC-5; top) and TB40/E (grown in ARPE-19; bottom). Infection by the trimer-only AD169 strain is restricted to PDGFRα-positive MRC-5 and ARPE-19RA lines. Viral inoculum was pre-incubated with sPDGFRα-Fc WT, sPDGFRα-Fc Y206S, sPDGFRα-Fc V242K, sPDGFRβ-Fc (at a single concentration of 100 nM), or hyperimmune globulin (HIG) prior to adding to cells. Data represent mean±SD, n=2 independent titrations.

Soluble PDGFRα-Fc potently neutralized both HCMV strains at nanomolar concentrations (FIG. 6). Neutralization by orthogonal sPDGFRα-Fc V242K was mostly indistinguishable from wild-type receptor and nearly complete at 1 to 10 nM (FIG. 6), demonstrating that virus binding and neutralization can indeed be successfully separated from growth factor interactions by just a single amino acid substitution. Soluble PDGFRα-Fc Y206S also neutralized but with reduced potency, consistent with the biochemical binding studies.

Discussion

Soluble PDGFRα as a prophylactic or treatment for HCMV is particularly promising due to exceptionally tight affinity for glycoprotein trimer and its ability to neutralize both trimer- and pentamer-mediated host cell entry. As described herein, deep mutagenesis was carried out to inform the engineering of PDGFRα variants that maintain tight virus binding but have lost growth factor interactions, and are thereby orthogonal to normal human signaling pathways. This is expected to improve both efficacy and safety in vivo, especially for the treatment of pregnant women and neonates.

Example 5: Materials and Methods

This example describes the materials and experimental procedures for the studies described in Examples 1-4.

Plasmids

Human PDGFRα isoform 1 (GenBank NM_006206.4; SEQ ID NO: 2) was cloned in to the NheI-XhoI sites of pCEP4 (Invitrogen) with a N-terminal HA leader (MKTIIALSYIFCLVFA; SEQ ID NO: 12), myc-tag, linker (GSPGGASG; SEQ ID NO: 13), and followed by the mature polypeptide (a.a. 24-1,089 of SEQ ID NO: 1). For measuring signaling activity, a minimal promoter under the control of tandem serum response elements was subcloned from SRE reporter vector 559 (Addgene #82686) (Reichhart et al., *Angew Chem Int Ed Engl* 55: 6339-6342, 2016), a GFP-PEST fluorescent reporter (Li et al., *J Biol Chem* 273: 34970-34975, 1998) was inserted at the AscI site, and the entire reporter cassette was inserted at the NruI site of pCEP4-myc-PDGFRα by Gibson assembly. As a negative control, human PDGFRβ isoform 1 (GenBank NM_002609.3; SEQ ID NO: 14) was similarly cloned between the NheI-XhoI sites of pCEP4 with a N-terminal HA leader, myc-tag, and linker that connects to the mature protein (a.a. 33-1,106 of SEQ ID NO: 14). No interactions between PDGFRβ and HCMV trimer were observed. Soluble PDGFRα-Fc was cloned into the NheI-XhoI sites of pcDNA3.1(+) (Invitrogen), and encompassed PDGFRα a.a. 1-524, a short connecting linker as outlined in FIG. 10A, and the C-terminus of human IgG1 (GenBank KY432415.1) beginning at either C220 or D221 as described in the Examples above. Alternatively, PDGFRα a.a. 1-524 were fused via linker GGGS (SEQ ID NO: 10) to D221-K447 of human IgG3 (GenBank P01860.2, SEQ ID NO: 15; this is an R435 allele with reduced binding to FcRn). Synthetic human codon-optimized gene fragments (Integrated DNA Technologies) for HCMV gO (GenBank ABV71596.1 for TB40/E strain, AJY56739.1 for Merlin strain) were genetically fused at the C-terminus to superfolder GFP (Pédelacq et al., *Nat Biotechnol* 24: 79-88, 2006) (for detection of soluble HCMV trimer binding to PDGFRα-positive cells) or to an 8-histidine tag (for expression of membrane-tethered HCMV trimer), and were ligated in to the NheI-XhoI sites of pcDNA3.1(+). Codon-optimized gene fragments for full-length HCMV gH (GenBank ABV71597.1 for TB40/E strain, YP 081523.1 for Merlin Strain) were cloned in to the NheI-XhoI sites of pcDNA3.1(+) for expression of membrane-tethered HCMV trimer. For production of soluble trimer, the extracellular region of gH with the leader peptide (a.a. 1-717 for TB40/E, a.a. 1-716 for Merlin) was subcloned with a 8-histidine tag. Codon-optimized synthetic genes for gL (GenBank ABV71629.1 for TB40/E strain, YP 081555.1 for Merlin) were cloned with C-terminal FLAG tags in to the NheI-XhoI sites of pcDNA3.1(+). Targeted mutations were made by overlap extension PCR. All plasmids were sequence verified (ACGT, Inc) and are deposited with Addgene.

Cells and Viruses

Expi293F cells (ThermoFisher), a suspension culture derivative of HEK293, were cultured in Expi293 Expression Medium (ThermoFisher) at 125 rpm, 8% $CO_2$, 37° C. MRC-5 embryonic lung fibroblasts and ARPE-19 adult retinal pigment epithelial cells from the American Type Culture Collection were grown at 37° C., 5% $CO_2$, in DMEM supplemented with 10% fetal bovine serum, 1 mM sodium pyruvate, 2 mM glutamax (Gibco), 10 mM Hepes pH 7.4, 0.1 mM MEM non-essential amino acids (Gibco), 100 units/ml penicillin G, and 100 μg/ml streptomycin sulfate. ARPE-19 ectopically expressing PDGFRα ("ARPE19-RA" cells) were generated by lentiviral transduction with pLV-EF1a-PDGFRα-IRES-PURO. HCMV virus stocks were prepared by electroporating purified bacmid DNA into either MRC-5 fibroblasts (AD169; (Yu et al., *J Virol* 76: 2316-2328, 2002) or ARPE-19 retinal pigment epithelial cells (TB40/E, clone BAC4; Sinzger et al., *J Gen Virol* 89: 359-368, 2008). Stocks were amplified twice by infecting cell monolayers in 15 cm tissue culture plates followed by 850 cm² roller bottles. Virions were concentrated 100× by centrifugation through a 20% sorbitol cushion, resuspended in phosphate-buffered saline (PBS) containing 1% BSA and 7% sucrose, and frozen at −80° C. Virus stocks were titered on MRC-5 and ARPE-19 cells by Immediate-Early Protein 1 (IE1) fluorescent focus assay (Zhu et al., J Virol 69: 7960-7970, 1995).

Flow Cytometry Analysis of Soluble HCMV Trimer Binding to Receptor

Soluble HCMV trimer was prepared by transfecting Expi293F cells at a density of $2\times10^6$/ml with 400 ng pcDNA3-gO-sfGFP, 400 ng pcDNA3-gH-8his and 400 ng pcDNA3-gL-FLAG per ml culture using Expifectamine (ThermoFisher). Transfection Enhancers (ThermoFisher) were added 18 hours later, and 4 days post-transfection the culture was centrifuged (1,000×g, 10 minutes, followed by a second spin of the supernatant at 21,000×g, 5 minutes). The medium supernatant was stored at −20° C. and used directly in binding experiments. Expi293F cells at $2\times10^6$/ml were transfected with plasmids encoding receptors (500 ng DNA per ml of culture) using Expifectamine. 24 hours post-transfection the cells were washed with PBS supplemented with 0.2% bovine serum albumin (PBS-BSA), incubated for 30 minutes on ice with anti-myc Alexa 647 (clone 9B11, 1/250 dilution; Cell Signaling Technology) and the indicated dilutions of gH/gL/gO-sfGFP-containing medium, washed twice with PBS-BSA, then analyzed on a BD LSR II flow cytometer. For competition assays, washed cells were pre-incubated with PDGF ligands (R&D Systems) for 2 minutes on ice prior to addition of gH/gL/gO-sfGFP-containing medium.

Deep Mutagenesis

The D2-D3 domains (a.a. D123-E311) within plasmid pCEP4-myc-PDGFRα were mutagenized by overlap extension PCR (Procko et al., J Mol Biol 2013; 425: 3563-3575) using primers with degenerate NNK codons. The plasmid library was transfected in to Expi293F cells using Expifectamine under conditions previously shown to typically give no more than a single coding variant per cell; 1 ng coding plasmid was diluted with 1,500 ng pCEP4-ACMV carrier plasmid per ml of cell culture at $2\times10^6$/ml, and the medium was replaced 2 hours post-transfection. The cells were collected after 24 hours, washed with ice-cold PBS-BSA, and incubated for 2 minutes on ice with PDGF-AA, -AB, -BB, and -CC (25 nM of each after addition of soluble trimer-containing medium) and anti-myc Alexa 647 (clone 9B11, 1/250 dilution; Cell Signaling Technology). Medium from cells expressing gH/gL/gO-sfGFP was then added to a final dilution of 1/3, and the cells were incubated on ice for 20 minutes. Cells were washed twice with PBS-BSA, and sorted on a BD FACS Aria II. The main cell population was gated by forward/side scattering to remove debris and doublets, and propidium iodide (1 μg/ml final) was added to the sample to exclude dead cells. Of the myc-positive (Alexa 647) population, the 15% of cells with the highest and lowest GFP fluorescence were collected (FIG. 1F) in tubes coated overnight with fetal bovine serum and containing Expi293 Expression Medium. Total RNA was extracted from the collected cells using a GeneJET RNA purification kit (Thermo Scientific), and cDNA was reverse transcribed with high fidelity Accuscript primed with a gene-specific oligonucleotide (RevTrans_PDGFRA_992R, TCATGCAGGTTGACAGCTTC; SEQ ID NO: 16). The diversified region of PDGFRα was PCR amplified as 3 fragments to provide full coverage of the D2-D3 domains during Illumina sequencing. During PCR, flanking sequences on the primers added adapters to the ends of the products for annealing to Illumina sequencing primers, unique barcoding, and for binding the flow cell. Amplicons were sequenced on an Illumina NovaSeq 6000 using a 2×250 nucleotide paired end protocol. Data were analyzed using Enrich (Fowler et al., Bioinformatics 2011; 27: 3430-3431), and commands are provided in the GEO deposit. Briefly, the frequencies of PDGFRα variants in the transcripts of the sorted populations were compared to their frequencies in the naive plasmid library to calculate an enrichment ratio.

Production of Soluble PDGFRα-Fc

Per ml of $2\times10^6$ Expi293F cells, 500 ng of pcDNA3-sPDGFRα-Fc (IgG1) and 3 μg of polyethylenimine (MW 25,000; Polysciences) were mixed in 100 μl of OptiMEM (Gibco) and incubated for 20 minutes at room temperature prior to adding to cells. Transfection Enhancers were added 18 hours post-transfection, and cells were cultured for six to seven days. Cells were removed by centrifugation at 600×g for 20 minutes at 4° C. Cell debris and precipitates were removed by centrifugation at 18,000×g for 25 minutes at 4° C. Supernatant was loaded on to KANEKA KanCapA 3G Affinity sorbent (Pall), and the resin was washed with PBS. Soluble PDGFRα-Fc was eluted with 60 mM sodium acetate pH 3.7, and 1 M Tris pH 8.0 was added to the eluate to neutralize the pH. Eluted sPDGFRα-Fc was concentrated with a centrifugal device (MWCO 100 kDa; Sartorius) and NaCl was added to 150 mM final. The protein was separated on a Superdex 200 Increase 10/300 GL (GE Healthcare Life Sciences) size exclusion chromatography column equilibrated with PBS. Peak fractions were pooled, concentrated, and stored at −80° C. after snap freezing in liquid nitrogen. The proteins were quantified by absorbance at 280 nm using calculated molar extinction coefficients for the monomeric mature polypeptides.

Fusions of sPDGFRα to the Fc region of IgG3 were expressed as described above, and the expression medium was dialyzed against water. Cell debris was removed by centrifugation at 18,000×g for 25 minutes at 4° C. Supernatant was loaded on to protein G HTC agarose beads (GoldBio) equilibrated with PBS. Protein was eluted with 100 mM glycine pH 2.5 and the eluate was neutralized by addition of 1 M Tris pH 9.0. Protein was further purified as described for the IgG1 fusions.

Flow Cytometry Analysis of PDGFRα-Fc Binding to HCMV Trimer on the Cell Surface 400 ng of each of pcDNA3-gH (full-length), pcDNA3-gL-FLAG and pcDNA3-gO-8his were transfected in to Expi293F cells at $2\times10^6$/ml using Expifectamine. Transfection Enhancers were added 22 hours later, and cells were harvested 46 hours post-transfection. Cells were washed with PBS-BSA and incubated with PDGFRα-Fc (purified as described) or PDGFRβ-Fc (R&D Systems) for 40 minutes on ice. Cells were then washed 3 times with PBS-BSA and stained with anti-FLAG M2-Cy3 (Sigma), chicken anti-HIS-FITC (polyclonal, Immunology Consultants Laboratory), and anti-human IgG-APC (clone HP6017, BioLegend) for 30 minutes on ice. Cells were washed three times with PBS-BSA and analyzed by flow cytometry. To compare data across different experiments, the change in ΔMFU for each condition was normalized to the ΔMFU at the maximum concentration of WT sPDGFRα-Fc: Relative binding= $(MFU_{sample}-MFU_{background})/(MFU_{max\ WT}-MFU_{background})$.

PDGFRα Signaling Assay 500 ng of PDGFRα reporter plasmid was transfected into 1 ml Expi293F cells at $2\times10^6$/ml using Expifectamine. 7.5 μl of 6 μM sPDGFRα-Fc (concentration based on monomer)

and 7.5 μl of 2 μM PDGF were mixed, incubated at room temperature for 40 minutes, and then added to 1 ml cells at transfection. Human gamma globulin was from Jackson Immuno Research Labs, and PDGFs were from R&D Systems. Cells were collected 24 hours post-transfection and stained with anti-myc-Alexa 647 to detect PDGFRα expression. GFP-PEST reporter expression was measured by flow-cytometry.

Virus Neutralization Assays

Neutralization assays were performed similarly to Stegmann et al. (*PLoS Pathog.* 2017 April; 13(4):e1006273) by serially diluting Fc-fused PDGFRα proteins or anti-HCMV immunoglobulin (Cytogam, CSL Behring) in PBS (vehicle) and incubating diluted proteins with HCMV virions for 1 hour at 37° C. Virion-protein mixtures were adsorbed onto target cells for 2 hours at 37° C., 5% $CO_2$, washed once with PBS, and infected cells were allowed to recover for 18 hours. The ability of each treatment to neutralize HCMV infection was measured using indirect-immunofluorescence by determining the number of cells expressing viral IE1, using anti-IE1 clone 1B12 (Zhu et al., *J Virol* 1995; 69: 7960-7970) and counterstaining nuclei with DAPI. A multiplicity of infection of 1 was used for AD169 infections, and a multiplicity of infection of 0.5 was used for TB40/E infections (based on stock titers acquired on MRC-5 fibroblasts).

Structural Modeling

The sequence of human PDGFRα was threaded onto the structure of PDGF-BB-bound PDGFRβ (PDB ID 3MJG; Shim et al., *Proc Natl Acad Sci USA*. 2010 Jun. 22; 107 (25):11307-11312), with one of the two receptor chains and the D1 domain removed. The model was minimized with ROSETTA using FastRelax (Leaver-Fay et al., *Meth Enzymol* 2011; 487: 545-574). Connectivity was determined using the AverageDegree filter in ROSETTA (Fleishman et al., *J Mol Biol.* 2011; 414: 289-302). Images were rendered with PyMOL (Schrödinger, LLC).

Reagent and Data Availability

Plasmids were deposited with Addgene. Raw and processed deep sequencing data were deposited in NCBI's Gene Expression Omnibus (GEO) under series accession number GSE138169.

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

---

The invention claimed is:

1. A modified platelet-derived growth factor receptor alpha (PDGFRα) polypeptide, comprising a human PDGFRα or an extracellular fragment thereof, wherein the polypeptide comprises at least one amino acid substitution relative to wild-type human PDGFRα of SEQ ID NO: 1, and retains the capacity to bind a cytomegalovirus (CMV) trimer comprised of glycoprotein H (gH), gL and gO, but exhibits reduced binding to one or more platelet-derived growth factor (PDGF) ligands compared to wild type PDGFRα, wherein the single amino acid substitution is selected from the group consisting of L137K, L137Q, Y206S, V242K and V242T.

2. The modified polypeptide of claim 1, wherein the single amino acid substitution is selected from the group consisting of Y206S and V242K.

3. An in vitro method of inhibiting CMV replication, comprising contacting the CMV with the modified polypeptide of claim 2.

4. A method of inhibiting CMV replication and/or spread in a subject, or a method of treating or inhibiting CMV infection in a subject, comprising administering to the subject a therapeutically effective amount of the modified polypeptide of claim 2, thereby inhibiting CMV replication and/or spread in the subject, or treating or inhibiting CMV infection in the subject.

5. The method of claim 4, wherein the subject is (i) a female subject who is pregnant; (ii) an infant whose mother is positive for CMV; (iii) a subject with an immunodeficiency; (iv) a transplant recipient; or (v) a subject who is immunosuppressed.

6. A composition comprising the modified polypeptide of claim 3 and a pharmaceutically acceptable carrier.

7. The modified polypeptide of claim 1, wherein the single amino acid substitution is V242K.

8. A composition comprising the modified polypeptide of claim 7 and a pharmaceutically acceptable carrier.

9. The modified polypeptide of claim 1, comprising full-length human PDGFRα.

10. The modified polypeptide of claim 1, wherein the polypeptide consists of an extracellular fragment of human PDGFRα.

11. The modified polypeptide of claim 10, wherein the extracellular fragment corresponds to residues 24 to 524 of human PDGFRα.

12. A fusion protein comprising the modified polypeptide of claim 1 and a heterologous polypeptide.

13. The fusion protein of claim 12, wherein the heterologous polypeptide is an Fc protein, a fluorescent protein, an enzyme, an antibody or antigen-binding protein, a cytokine, a cellular ligand or receptor, or serum albumin.

14. A composition comprising the modified polypeptide of claim 1 and a pharmaceutically acceptable carrier.

* * * * *

SEQUENCE LISTING

```
<160> NUMBER OF SEQ ID NOS: 17

<210> SEQ ID NO 1
<211> LENGTH: 1089
<212> TYPE: PRT
<213> ORGANISM: Homo sapiens

<400> SEQUENCE: 1

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
            115                 120                 125

Val Pro Leu Gly Met Thr Asp Tyr Leu Val Ile Val Glu Asp Asp Asp
        130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
```

-continued

```
                195                200                205
Lys Ala Thr Ser Glu Leu Asp Leu Glu Met Glu Ala Leu Lys Thr Val
    210                215                220
Tyr Lys Ser Gly Glu Thr Ile Val Val Thr Cys Ala Val Phe Asn Asn
225                230                235                240
Glu Val Val Asp Leu Gln Trp Thr Tyr Pro Gly Glu Val Lys Gly Lys
                245                250                255
Gly Ile Thr Met Leu Glu Glu Ile Lys Val Pro Ser Ile Lys Leu Val
                260                265                270
Tyr Thr Leu Thr Val Pro Glu Ala Thr Val Lys Asp Ser Gly Asp Tyr
            275                280                285
Glu Cys Ala Ala Arg Gln Ala Thr Arg Glu Val Lys Glu Met Lys Lys
        290                295                300
Val Thr Ile Ser Val His Glu Lys Gly Phe Ile Glu Ile Lys Pro Thr
305                310                315                320
Phe Ser Gln Leu Glu Ala Val Asn Leu His Glu Val Lys His Phe Val
                325                330                335
Val Glu Val Arg Ala Tyr Pro Pro Pro Arg Ile Ser Trp Leu Lys Asn
            340                345                350
Asn Leu Thr Leu Ile Glu Asn Leu Thr Glu Ile Thr Thr Asp Val Glu
        355                360                365
Lys Ile Gln Glu Ile Arg Tyr Arg Ser Lys Leu Lys Leu Ile Arg Ala
    370                375                380
Lys Glu Glu Asp Ser Gly His Tyr Thr Ile Val Ala Gln Asn Glu Asp
385                390                395                400
Ala Val Lys Ser Tyr Thr Phe Glu Leu Leu Thr Gln Val Pro Ser Ser
                405                410                415
Ile Leu Asp Leu Val Asp Asp His His Gly Ser Thr Gly Gly Gln Thr
            420                425                430
Val Arg Cys Thr Ala Glu Gly Thr Pro Leu Pro Asp Ile Glu Trp Met
        435                440                445
Ile Cys Lys Asp Ile Lys Lys Cys Asn Asn Glu Thr Ser Trp Thr Ile
    450                455                460
Leu Ala Asn Asn Val Ser Asn Ile Ile Thr Glu Ile His Ser Arg Asp
465                470                475                480
Arg Ser Thr Val Glu Gly Arg Val Thr Phe Ala Lys Val Glu Glu Thr
                485                490                495
Ile Ala Val Arg Cys Leu Ala Lys Asn Leu Leu Gly Ala Glu Asn Arg
            500                505                510
Glu Leu Lys Leu Val Ala Pro Thr Leu Arg Ser Glu Leu Thr Val Ala
        515                520                525
Ala Ala Val Leu Val Leu Leu Val Ile Val Ile Ile Ser Leu Ile Val
    530                535                540
Leu Val Val Ile Trp Lys Gln Lys Pro Arg Tyr Glu Ile Arg Trp Arg
545                550                555                560
Val Ile Glu Ser Ile Ser Pro Asp Gly His Glu Tyr Ile Tyr Val Asp
                565                570                575
Pro Met Gln Leu Pro Tyr Asp Ser Arg Trp Glu Phe Pro Arg Asp Gly
            580                585                590
Leu Val Leu Gly Arg Val Leu Gly Ser Gly Ala Phe Gly Lys Val Val
            595                600                605
Glu Gly Thr Ala Tyr Gly Leu Ser Arg Ser Gln Pro Val Met Lys Val
    610                615                620
```

-continued

```
Ala Val Lys Met Leu Lys Pro Thr Ala Arg Ser Ser Glu Lys Gln Ala
625             630             635             640

Leu Met Ser Glu Leu Lys Ile Met Thr His Leu Gly Pro His Leu Asn
            645             650             655

Ile Val Asn Leu Leu Gly Ala Cys Thr Lys Ser Gly Pro Ile Tyr Ile
            660             665             670

Ile Thr Glu Tyr Cys Phe Tyr Gly Asp Leu Val Asn Tyr Leu His Lys
            675             680             685

Asn Arg Asp Ser Phe Leu Ser His His Pro Glu Lys Pro Lys Lys Glu
            690             695             700

Leu Asp Ile Phe Gly Leu Asn Pro Ala Asp Glu Ser Thr Arg Ser Tyr
705             710             715             720

Val Ile Leu Ser Phe Glu Asn Asn Gly Asp Tyr Met Asp Met Lys Gln
            725             730             735

Ala Asp Thr Thr Gln Tyr Val Pro Met Leu Glu Arg Lys Glu Val Ser
            740             745             750

Lys Tyr Ser Asp Ile Gln Arg Ser Leu Tyr Asp Arg Pro Ala Ser Tyr
            755             760             765

Lys Lys Lys Ser Met Leu Asp Ser Glu Val Lys Asn Leu Leu Ser Asp
            770             775             780

Asp Asn Ser Glu Gly Leu Thr Leu Leu Asp Leu Leu Ser Phe Thr Tyr
785             790             795             800

Gln Val Ala Arg Gly Met Glu Phe Leu Ala Ser Lys Asn Cys Val His
            805             810             815

Arg Asp Leu Ala Ala Arg Asn Val Leu Leu Ala Gln Gly Lys Ile Val
            820             825             830

Lys Ile Cys Asp Phe Gly Leu Ala Arg Asp Ile Met His Asp Ser Asn
            835             840             845

Tyr Val Ser Lys Gly Ser Thr Phe Leu Pro Val Lys Trp Met Ala Pro
    850             855             860

Glu Ser Ile Phe Asp Asn Leu Tyr Thr Thr Leu Ser Asp Val Trp Ser
865             870             875             880

Tyr Gly Ile Leu Leu Trp Glu Ile Phe Ser Leu Gly Gly Thr Pro Tyr
            885             890             895

Pro Gly Met Met Val Asp Ser Thr Phe Tyr Asn Lys Ile Lys Ser Gly
            900             905             910

Tyr Arg Met Ala Lys Pro Asp His Ala Thr Ser Glu Val Tyr Glu Ile
            915             920             925

Met Val Lys Cys Trp Asn Ser Glu Pro Glu Lys Arg Pro Ser Phe Tyr
    930             935             940

His Leu Ser Glu Ile Val Glu Asn Leu Leu Pro Gly Gln Tyr Lys Lys
945             950             955             960

Ser Tyr Glu Lys Ile His Leu Asp Phe Leu Lys Ser Asp His Pro Ala
            965             970             975

Val Ala Arg Met Arg Val Asp Ser Asp Asn Ala Tyr Ile Gly Val Thr
            980             985             990

Tyr Lys Asn Glu Glu Asp Lys Leu  Lys Asp Trp Glu Gly  Gly Leu Asp
            995             1000            1005

Glu Gln  Arg Leu Ser Ala Asp  Ser Gly Tyr Ile Ile  Pro Leu Pro
    1010            1015            1020

Asp Ile  Asp Pro Val Pro Glu  Glu Glu Asp Leu Gly  Lys Arg Asn
    1025            1030            1035
```

-continued

| Arg His | Ser Ser Gln Thr Ser | Glu Glu Ser Ala Ile | Glu Thr Gly |
|---|---|---|---|
| 1040 | 1045 | 1050 | |

| Ser Ser | Ser Ser Thr Phe Ile | Lys Arg Glu Asp Glu | Thr Ile Glu |
|---|---|---|---|
| 1055 | 1060 | 1065 | |

| Asp Ile | Asp Met Met Asp Asp | Ile Gly Ile Asp Ser | Ser Asp Leu |
|---|---|---|---|
| 1070 | 1075 | 1080 | |

| Val Glu | Asp Ser Phe Leu |
|---|---|
| 1085 | |

```
<210> SEQ ID NO 2
<211> LENGTH: 3270
<212> TYPE: DNA
<213> ORGANISM: Homo sapiens

<400> SEQUENCE: 2
atggggactt cccatccggc gttcctggtc ttaggctgtc ttctcacagg gctgagccta      60
atcctctgcc agctttcatt accctctatc cttccaaatg aaaatgaaaa ggttgtgcag     120
ctgaattcat ccttttctct gagatgcttt ggggagagtg aagtgagctg gcagtacccc     180
atgtctgaag aagagagctc cgatgtggaa atcagaaatg aagaaaacaa cagcggcctt     240
tttgtgacgg tcttggaagt gagcagtgcc tcggcggccc acacagggtt gtacacttgc     300
tattacaacc acactcagac agaagagaat gagcttgaag gcaggcacat ttacatctat     360
gtgccagacc cagatgtagc ctttgtacct ctaggaatga cggattattt agtcatcgtg     420
gaggatgatg attctgccat tataccttgt cgcacaactg atcccgagac tcctgtaacc     480
ttacacaaca gtgagggggt ggtacctgcc tcctacgaca gcagacaggg ctttaatggg     540
accttcactg tagggcccta tatctgtgag gccaccgtca aaggaaagaa gttccagacc     600
atcccattta atgtttatgc tttaaaagca acatcagagc tggatctaga aatggaagct     660
cttaaaaccg tgtataagtc aggggaaacg attgtggtca cctgtgctgt ttttaacaat     720
gaggtggttg accttcaatg gacttaccct ggagaagtga aaggcaaagg catcacaatg     780
ctggaagaaa tcaaagtccc atccatcaaa ttggtgtaca cttttgacgg tccccgaggcc     840 acggtgaaag acagtggaga ttacgaatgt gctgcccgcc aggctaccag ggaggtcaaa     900
gaaatgaaga aagtcactat ttctgtccat gagaaaggtt tcattgaaat caaacccacc     960
ttcagccagt tggaagctgt caacctgcat gaagtcaaac attttgttgt agaggtgcgg    1020
gcctacccac ctcccaggat atcctggctg aaaaacaatc tgactctgat tgaaaatctc    1080
actgagatca ccactgatgt ggaaaagatt caggaaataa ggtatcgaag caaattaaag    1140
ctgatccgtg ctaaggaaga agacagtggc cattatacta ttgtagctca aaatgaagat    1200
gctgtgaaga ctatacttttt gaactgtta actcaagttc cttcatccat tctggacttg    1260
gtcgatgatc accatggctc aactggggga cagacggtga ggtgcacagc tgaaggcacg    1320
ccgcttcctg atattgagtg gatgatatgc aaagatatta gaaatgtaa taatgaaact    1380 tcctggacta ttttggccaa caatgtctca aacatcatca cggagatcca ctcccgagac    1440
aggagtaccg tggagggccg tgtgactttc gccaaagtgg aggagaccat cgccgtgcga    1500
tgcctggcta agaatctcct ggagctgag aaccgagagc tgaagctggt ggctcccacc    1560
ctgcgttctg aactcacggt ggctgctgca gtcctggtgc tgttggtgat tgtgatcatc    1620
tcacttattg tcctggttgt catttggaaa cagaaaccga ggtatgaaat tcgctggagg    1680
gtcattgaat caatcagccc agatggacat gaatatattt atgtggaccc gatgcagctg    1740
ccttatgact caagatggga gtttccaaga gatggactag tgcttggtcg ggtcttgggg    1800
```

```
tctggagcgt ttgggaaggt ggttgaagga acagcctatg gattaagccg gtcccaacct    1860
gtcatgaaag ttgcagtgaa gatgctaaaa cccacggcca gatccagtga aaaacaagct    1920
ctcatgtctg aactgaagat aatgactcac ctggggccac atttgaacat tgtaaacttg    1980
ctgggagcct gcaccaagtc aggcccccatt tacatcatca cagagtattg cttctatgga    2040
gatttggtca actatttgca taagaatagg gatagcttcc tgagccacca cccagagaag    2100
ccaaagaaag agctggatat ctttggattg aaccctgctg atgaaagcac acggagctat    2160
gttattttat cttttgaaaa caatggtgac tacatggaca tgaagcaggc tgatactaca    2220
cagtatgtcc ccatgctaga aaggaaagag gtttctaaat attccgacat ccagagatca    2280
ctctatgatc gtccagcctc atataagaag aaatctatgt tagactcaga agtcaaaaac    2340
ctcctttcag atgataactc agaaggcctt actttattgg atttgttgag cttcacctat    2400
caagttgccc gaggaatgga gttttttggct tcaaaaaatt gtgtccaccg tgatctggct    2460
gctcgcaacg tcctcctggc acaaggaaaa attgtgaaga tctgtgactt tggcctggcc    2520
agagacatca tgcatgattc gaactatgtg tcgaaaggca gtaccttctt gcccgtgaag    2580
tggatggctc ctgagagcat ctttgacaac ctctacacca cactgagtga tgtctggtct    2640
tatggcattc tgctctggga gatctttttcc cttggtggca cccccttaccc cggcatgatg    2700 gtggattcta ctttctacaa taagatcaag agtgggtacc ggatggccaa gcctgaccac    2760
gctaccagtg aagtctacga gatcatggtg aaatgctgga cagtgagcc ggagaagaga    2820 ccctcctttt accacctgag tgagattgtg gagaatctgc tgcctggaca atataaaaag    2880
agttatgaaa aaattcacct ggacttcctg aagagtgacc atcctgctgt ggcacgcatg    2940
cgtgtggact cagacaatgc atacattggt gtcacctaca aaaacgagga agacaagctg    3000
aaggactggg agggtggtct ggatgagcag agactgagcg ctgacagtgg ctacatcatt    3060
cctctgcctg acattgaccc tgtccctgag gaggaggacc tgggcaagag gaacagacac    3120
agctcgcaga cctctgaaga gagtgccatt gagacgggtt ccagcagttc caccttcatc    3180
aagagagagg acgagaccat tgaagacatc gacatgatgg atgacatcgg catagactct    3240
tcagacctgg tggaagacag cttcctgtaa                                      3270
```

```
<210> SEQ ID NO 3
<211> LENGTH: 464
<212> TYPE: PRT
<213> ORGANISM: cytomegalovirus

<400> SEQUENCE: 3

Met Gly Arg Lys Glu Asp Met Arg Ser Ile Ser Lys Leu Phe Phe Ile
1               5                   10                  15

Ile Ser Leu Thr Val Leu Leu Phe Ser Ile Ile Asn Cys Lys Val Val
                20                  25                  30

Arg Pro Pro Gly Arg Tyr Trp Leu Gly Thr Val Leu Ser Thr Ile Gly
            35                  40                  45

Lys Gln Lys Leu Asp Lys Phe Lys Leu Glu Ile Leu Lys Gln Leu Glu
        50                  55                  60

Arg Glu Pro Tyr Thr Lys Tyr Phe Asn Met Thr Arg Gln His Val Lys
65                  70                  75                  80

Asn Leu Thr Met Asn Met Thr Gln Phe Pro Gln Tyr Tyr Ile Leu Ala
                85                  90                  95

Gly Pro Ile Arg Asn Asp Ser Ile Thr Tyr Leu Trp Phe Asp Phe Tyr
            100                 105                 110
```

-continued

```
Ser Thr Gln Leu Arg Lys Pro Ala Lys Tyr Val Tyr Ser Gln Tyr Asn
        115                 120                 125

His Thr Ala Lys Thr Ile Thr Phe Arg Pro Pro Ser Cys Gly Thr Val
    130                 135                 140

Pro Ser Met Thr Cys Leu Ser Glu Met Leu Asn Val Ser Lys Arg Asn
145                 150                 155                 160

Asp Thr Gly Glu Gln Gly Cys Gly Asn Phe Thr Thr Phe Asn Pro Met
                165                 170                 175

Phe Phe Asn Val Pro Arg Trp Asn Thr Lys Leu Tyr Val Gly Pro Thr
                180                 185                 190

Lys Val Asn Val Asp Ser Gln Thr Ile Tyr Phe Leu Gly Leu Thr Ala
                195                 200                 205

Leu Leu Leu Arg Tyr Ala Gln Arg Asn Cys Thr His Ser Phe Tyr Leu
        210                 215                 220

Val Asn Ala Met Ser Arg Asn Leu Phe Arg Val Pro Lys Tyr Ile Asn
225                 230                 235                 240

Gly Thr Lys Leu Lys Asn Thr Met Arg Lys Leu Lys Arg Lys Gln Ala
                245                 250                 255

Pro Val Lys Glu Gln Leu Glu Lys Lys Thr Lys Lys Ser Gln Ser Thr
                260                 265                 270

Thr Thr Pro Tyr Phe Ser Tyr Thr Thr Ser Thr Ala Leu Asn Val Thr
        275                 280                 285

Thr Asn Ala Thr Tyr Arg Val Thr Thr Ser Ala Lys Arg Ile Pro Thr
        290                 295                 300

Ser Thr Ile Ala Tyr Arg Pro Asp Ser Ser Phe Met Lys Ser Ile Met
305                 310                 315                 320

Ala Thr Gln Leu Arg Asp Leu Ala Thr Trp Val Tyr Thr Thr Leu Arg
                325                 330                 335

Tyr Arg Asn Glu Pro Phe Cys Lys Pro Asp Arg Asn Arg Thr Ala Val
                340                 345                 350

Ser Glu Phe Met Lys Asn Thr His Val Leu Ile Arg Asn Glu Thr Pro
        355                 360                 365

Tyr Thr Ile Tyr Gly Thr Leu Asp Met Ser Ser Leu Tyr Tyr Asn Glu
        370                 375                 380

Thr Met Ser Val Glu Asn Glu Thr Ala Ser Asp Asn Asn Glu Thr Thr
385                 390                 395                 400

Pro Thr Ser Pro Ser Thr Arg Phe Gln Lys Thr Phe Ile Asp Pro Leu
                405                 410                 415

Trp Asp Tyr Leu Asp Ser Leu Leu Phe Leu Asp Lys Ile Arg Asn Phe
                420                 425                 430

Ser Leu Gln Leu Pro Ala Tyr Gly Asn Leu Thr Pro Pro Glu His Arg
        435                 440                 445

Arg Ala Val Asn Leu Ser Thr Leu Asn Ser Leu Trp Trp Trp Leu Gln
    450                 455                 460
```

```
<210> SEQ ID NO 4
<211> LENGTH: 743
<212> TYPE: PRT
<213> ORGANISM: cytomegalovirus

<400> SEQUENCE: 4

Met Arg Pro Gly Leu Pro Phe Tyr Leu Thr Val Phe Ala Val Tyr Leu
1               5                   10                  15

Leu Ser His Leu Pro Ser Gln Arg Tyr Gly Ala Asp Ala Ala Ser Glu
```

-continued

```
                20                  25                  30

Ala Leu Asp Pro His Ala Phe His Leu Leu Leu Asn Thr Tyr Gly Arg
             35                  40                  45

Pro Ile Arg Phe Leu Arg Glu Asn Thr Thr Gln Cys Thr Tyr Asn Ser
         50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                 85                  90                  95

Leu Phe Ala Gly Pro Leu Ala Glu Gln Phe Leu Asn Gln Val Asp Leu
                100                 105                 110

Thr Glu Thr Leu Glu Arg Tyr Gln Gln Arg Leu Asn Thr Tyr Ala Leu
            115                 120                 125

Val Ser Lys Asp Leu Ala Ser Tyr Arg Ser Phe Ser Gln Gln Leu Lys
        130                 135                 140

Ala Gln Asp Ser Leu Gly Gln Gln Pro Thr Thr Val Pro Pro Pro Ile
145                 150                 155                 160

Asp Leu Ser Ile Pro His Val Trp Met Pro Pro Gln Thr Thr Pro His
                165                 170                 175

Asp Trp Lys Gly Ser His Thr Thr Ser Gly Leu His Arg Pro His Phe
            180                 185                 190

Asn Gln Thr Cys Ile Leu Phe Asp Gly His Asp Leu Leu Phe Ser Thr
            195                 200                 205

Val Thr Pro Cys Leu His Gln Gly Phe Tyr Leu Met Asp Glu Leu Arg
        210                 215                 220

Tyr Val Lys Ile Thr Leu Thr Glu Asp Phe Phe Val Val Thr Val Ser
225                 230                 235                 240

Ile Asp Asp Asp Thr Pro Met Leu Leu Ile Phe Gly His Leu Pro Arg
                245                 250                 255

Val Leu Phe Lys Ala Pro Tyr Gln Arg Asp Asn Phe Ile Leu Arg Gln
            260                 265                 270

Thr Glu Lys His Glu Leu Leu Val Leu Val Lys Lys Thr Gln Leu Asn
        275                 280                 285

Arg His Ser Tyr Leu Lys Asp Ser Asp Phe Leu Asp Ala Ala Leu Asp
    290                 295                 300

Phe Asn Tyr Leu Asp Leu Ser Ala Leu Leu Arg Asn Ser Phe His Arg
305                 310                 315                 320

Tyr Ala Val Asp Val Leu Lys Ser Gly Arg Cys Gln Met Leu Asp Arg
            325                 330                 335

Arg Thr Val Glu Met Ala Phe Ala Tyr Ala Leu Ala Leu Phe Ala Ala
            340                 345                 350

Ala Arg Gln Glu Glu Ala Gly Thr Glu Ile Ser Ile Pro Arg Ala Leu
            355                 360                 365

Asp Arg Gln Ala Ala Leu Leu Gln Ile Gln Glu Phe Met Ile Thr Cys
        370                 375                 380

Leu Ser Gln Thr Pro Pro Arg Thr Thr Leu Leu Leu Tyr Pro Thr Ala
385                 390                 395                 400

Val Asp Leu Ala Lys Arg Ala Leu Trp Thr Pro Asp Gln Ile Thr Asp
            405                 410                 415

Ile Thr Ser Leu Val Arg Leu Val Tyr Ile Leu Ser Lys Gln Asn Gln
            420                 425                 430

Gln His Leu Ile Pro Gln Trp Ala Leu Arg Gln Ile Ala Asp Phe Ala
            435                 440                 445
```

-continued

```
Leu Gln Leu His Lys Thr His Leu Ala Ser Phe Leu Ser Ala Phe Ala
    450             455             460

Arg Gln Glu Leu Tyr Leu Met Gly Ser Leu Val His Ser Met Leu Val
465             470             475             480

His Thr Thr Glu Arg Arg Glu Ile Phe Ile Val Glu Thr Gly Leu Cys
            485             490             495

Ser Leu Ala Glu Leu Ser His Phe Thr Gln Leu Leu Ala His Pro His
            500             505             510

His Glu Tyr Leu Ser Asp Leu Tyr Thr Pro Cys Ser Ser Ser Gly Arg
            515             520             525

Arg Asp His Ser Leu Glu Arg Leu Thr Arg Leu Phe Pro Asp Ala Thr
    530             535             540

Val Pro Ala Thr Val Pro Ala Ala Leu Ser Ile Leu Ser Thr Met Gln
545             550             555             560

Pro Ser Thr Leu Glu Thr Phe Pro Asp Leu Phe Cys Leu Pro Leu Gly
            565             570             575

Glu Ser Phe Ser Ala Leu Thr Val Ser Glu His Val Ser Tyr Val Val
            580             585             590

Thr Asn Gln Tyr Leu Ile Lys Gly Ile Ser Tyr Pro Val Ser Thr Thr
    595             600             605

Val Val Gly Gln Ser Leu Ile Ile Thr Gln Thr Asp Ser Gln Ser Lys
    610             615             620

Cys Glu Leu Thr Arg Asn Met His Thr Thr His Ser Ile Thr Ala Ala
625             630             635             640

Leu Asn Ile Ser Leu Glu Asn Cys Ala Phe Cys Gln Ser Ala Leu Leu
            645             650             655

Glu Tyr Asp Asp Thr Gln Gly Val Ile Asn Ile Met Tyr Met His Asp
            660             665             670

Ser Asp Asp Val Leu Phe Ala Leu Asp Pro Tyr Asn Glu Val Val Val
    675             680             685

Ser Ser Pro Arg Thr His Tyr Leu Met Leu Leu Lys Asn Gly Thr Val
    690             695             700

Leu Glu Val Thr Asp Val Val Val Asp Ala Thr Asp Ser Arg Leu Leu
705             710             715             720

Met Met Ser Val Tyr Ala Leu Ser Ala Ile Ile Gly Ile Tyr Leu Leu
            725             730             735

Tyr Arg Met Leu Lys Thr Cys
            740
```

```
<210> SEQ ID NO 5
<211> LENGTH: 278
<212> TYPE: PRT
<213> ORGANISM: cytomegalovirus

<400> SEQUENCE: 5

Met Cys Arg Arg Pro Asp Cys Gly Phe Ser Phe Ser Pro Gly Pro Val
1               5               10              15

Val Leu Leu Trp Cys Cys Leu Leu Leu Pro Ile Val Ser Ser Val Ala
            20              25              30

Val Ser Val Ala Pro Thr Ala Ala Glu Lys Val Pro Ala Glu Cys Pro
            35              40              45

Glu Leu Thr Arg Arg Cys Leu Leu Gly Glu Val Phe Gln Gly Asp Lys
    50              55              60

Tyr Glu Ser Trp Leu Arg Pro Leu Val Asn Val Thr Gly Arg Asn Gly
```

-continued

```
65                  70                  75                  80

Pro Leu Ser Gln Leu Ile Arg Tyr Arg Pro Val Thr Pro Glu Ala Ala
                85                  90                  95

Asn Ser Val Leu Leu Asp Asp Ala Phe Leu Asp Thr Leu Ala Leu Leu
               100                 105                 110

Tyr Asn Asn Pro Asp Gln Leu Arg Ala Leu Leu Thr Leu Leu Ser Ser
               115                 120                 125

Asp Thr Ala Pro Arg Trp Met Thr Val Met Arg Gly Tyr Ser Glu Cys
   130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
               165                 170                 175

His Val Leu Gly Phe Glu Leu Val Pro Pro Ser Leu Phe Asn Val Val
               180                 185                 190

Val Ala Ile Arg Asn Glu Ala Thr Arg Thr Asn Arg Ala Val Arg Leu
               195                 200                 205

Pro Val Ser Thr Ala Ala Ala Pro Glu Gly Ile Thr Leu Phe Tyr Gly
   210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
               245                 250                 255

Leu Lys Gln Thr Arg Val Asn Leu Pro Ala His Ser Arg Tyr Gly Pro
               260                 265                 270

Gln Ala Val Asp Ala Arg
               275
```

```
<210> SEQ ID NO 6
<211> LENGTH: 472
<212> TYPE: PRT
<213> ORGANISM: cytomegalovirus

<400> SEQUENCE: 6

Met Gly Lys Lys Glu Met Ile Met Val Lys Gly Ile Pro Lys Ile Met
1               5                  10                  15

Leu Leu Ile Ser Ile Thr Phe Leu Leu Leu Ser Leu Ile Asn Cys Asn
               20                  25                  30

Val Leu Val Asn Ser Arg Gly Thr Arg Arg Ser Trp Pro Tyr Thr Val
               35                  40                  45

Leu Ser Tyr Arg Gly Lys Glu Ile Leu Lys Lys Gln Lys Glu Asp Ile
   50                  55                  60

Leu Lys Arg Leu Met Ser Thr Ser Ser Asp Gly Tyr Arg Phe Leu Met
65                  70                  75                  80

Tyr Pro Ser Gln Gln Lys Phe His Ala Ile Val Ile Ser Met Asp Lys
               85                  90                  95

Phe Pro Gln Asp Tyr Ile Leu Ala Gly Pro Ile Arg Asn Asp Ser Ile
               100                 105                 110

Thr His Met Trp Phe Asp Phe Tyr Ser Thr Gln Leu Arg Lys Pro Ala
               115                 120                 125

Lys Tyr Val Tyr Ser Glu Tyr Asn His Thr Ala His Lys Ile Thr Leu
               130                 135                 140

Arg Pro Pro Pro Cys Gly Thr Val Pro Ser Met Asn Cys Leu Ser Glu
145                 150                 155                 160
```

-continued

```
Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
            180                 185                 190

Thr Lys Leu Tyr Ile Gly Ser Asn Lys Val Asn Val Asp Ser Gln Thr
        195                 200                 205

Ile Tyr Phe Leu Gly Leu Thr Ala Leu Leu Leu Arg Tyr Ala Gln Arg
    210                 215                 220

Asn Cys Thr Arg Ser Phe Tyr Leu Val Asn Ala Met Ser Arg Asn Leu
225                 230                 235                 240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
            260                 265                 270

Lys Asn Lys Lys Ser Gln Ser Thr Thr Thr Pro Tyr Leu Ser Tyr Thr
        275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305                 310                 315                 320

Ser Asn Phe Met Lys Ser Ile Met Ala Thr Gln Leu Arg Asp Leu Ala
                325                 330                 335

Thr Trp Val Tyr Thr Thr Leu Arg Tyr Arg Asn Glu Pro Phe Cys Lys
            340                 345                 350

Pro Asp Arg Asn Arg Thr Ala Val Ser Glu Phe Met Lys Asn Thr His
            355                 360                 365

Val Leu Ile Arg Asn Glu Thr Pro Tyr Thr Ile Tyr Gly Thr Leu Asp
    370                 375                 380

Met Ser Ser Leu Tyr Tyr Asn Glu Thr Met Ser Val Glu Asn Glu Thr
385                 390                 395                 400

Ala Ser Asp Asn Asn Glu Thr Thr Pro Thr Ser Pro Ser Thr Arg Phe
                405                 410                 415

Gln Arg Thr Phe Ile Asp Pro Leu Trp Asp Tyr Leu Asp Ser Leu Leu
            420                 425                 430

Phe Leu Asp Lys Ile Arg Asn Phe Ser Leu Gln Leu Pro Ala Tyr Gly
        435                 440                 445

Asn Leu Thr Pro Pro Glu His Arg Arg Ala Ala Asn Leu Ser Thr Leu
    450                 455                 460

Asn Ser Leu Trp Trp Trp Ser Gln
465                 470

<210> SEQ ID NO 7
<211> LENGTH: 742
<212> TYPE: PRT
<213> ORGANISM: cytomegalovirus

<400> SEQUENCE: 7

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60
```

```
Leu Arg Asn Ser Thr Val Val Arg Glu Asn Ala Ile Ser Phe Asn Phe
65              70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
        130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
                180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
        210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
            275                 280                 285

His Ser Tyr Leu Lys Asp Pro Asp Phe Leu Asp Ala Ala Leu Asp Phe
        290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
        370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
            405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
        450                 455                 460

Gln Glu Leu Tyr Leu Met Gly Ser Leu Val His Ser Met Leu Val His
465                 470                 475                 480
```

-continued

```
Thr Thr Glu Arg Arg Glu Ile Phe Ile Val Glu Thr Gly Leu Cys Ser
            485             490             495

Leu Ala Glu Leu Ser His Phe Thr Gln Leu Leu Ala His Pro His His
        500             505             510

Glu Tyr Leu Ser Asp Leu Tyr Thr Pro Cys Ser Ser Ser Gly Arg Arg
        515             520             525

Asp His Ser Leu Glu Arg Leu Thr Arg Leu Phe Pro Asp Ala Thr Val
    530             535             540

Pro Ala Thr Val Pro Ala Ala Leu Ser Ile Leu Ser Thr Met Gln Pro
545             550             555             560

Ser Thr Leu Glu Thr Phe Pro Asp Leu Phe Cys Leu Pro Leu Gly Glu
            565             570             575

Ser Phe Ser Ala Leu Thr Val Ser Glu His Val Ser Tyr Ile Val Thr
            580             585             590

Asn Gln Tyr Leu Ile Lys Gly Ile Ser Tyr Pro Val Ser Thr Thr Val
        595             600             605

Val Gly Gln Ser Leu Ile Ile Thr Gln Thr Asp Ser Gln Thr Lys Cys
    610             615             620

Glu Leu Thr Arg Asn Met His Thr Thr His Ser Ile Thr Val Ala Leu
625             630             635             640

Asn Ile Ser Leu Glu Asn Cys Ala Phe Cys Gln Ser Ala Leu Leu Glu
            645             650             655

Tyr Asp Asp Thr Gln Gly Val Ile Asn Ile Met Tyr Met His Asp Ser
            660             665             670

Asp Asp Val Leu Phe Ala Leu Asp Pro Tyr Asn Glu Val Val Val Ser
            675             680             685

Ser Pro Arg Thr His Tyr Leu Met Leu Leu Lys Asn Gly Thr Val Leu
        690             695             700

Glu Val Thr Asp Val Val Val Asp Ala Thr Asp Ser Arg Leu Leu Met
705             710             715             720

Met Ser Val Tyr Ala Leu Ser Ala Ile Ile Gly Ile Tyr Leu Leu Tyr
            725             730             735

Arg Met Leu Lys Thr Cys
            740
```

<210> SEQ ID NO 8
<211> LENGTH: 278
<212> TYPE: PRT
<213> ORGANISM: cytomegalovirus

<400> SEQUENCE: 8

```
Met Cys Arg Arg Pro Asp Cys Gly Phe Ser Phe Ser Pro Gly Pro Val
1               5               10              15

Ile Leu Leu Trp Cys Cys Leu Leu Leu Pro Ile Val Ser Ser Ala Ala
            20              25              30

Val Ser Val Ala Pro Thr Ala Ala Glu Lys Val Pro Ala Glu Cys Pro
        35              40              45

Glu Leu Thr Arg Arg Cys Leu Leu Gly Glu Val Phe Glu Gly Asp Lys
    50              55              60

Tyr Glu Ser Trp Leu Arg Pro Leu Val Asn Val Thr Gly Arg Asp Gly
65              70              75              80

Pro Leu Ser Gln Leu Ile Arg Tyr Arg Pro Val Thr Pro Glu Ala Ala
            85              90              95

Asn Ser Val Leu Leu Asp Glu Ala Phe Leu Asp Thr Leu Ala Leu Leu
            100             105             110
```

-continued

```
Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
                180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
        210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
                260                 265                 270

Gln Ala Val Asp Ala Arg
        275

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Ile Glu Gly Arg Met Asp
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Gly Gly Gly Ser
1

<210> SEQ ID NO 11
<211> LENGTH: 455
<212> TYPE: PRT
<213> ORGANISM: Homo sapiens

<400> SEQUENCE: 11

Gln Val Gln Leu Val Glu Ser Gly Gly Gly Ala Val Gln Pro Gly Arg
1               5                   10                  15

Ser Leu Arg Leu Ser Cys Ala Ala Ala Gly Phe Ser Phe Ser Asp Thr
                20                  25                  30

Gly Met His Trp Val Arg Gln Ala Pro Gly Lys Gly Leu Glu Trp Val
        35                  40                  45

Ala Val Ile Ser Phe Asp Gly Ser Lys Gln Ser Tyr Gly Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Arg Leu Ala Val Phe Gly Tyr Tyr Asn Thr Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Arg Val Glu
        210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
        450                 455
```

```
<210> SEQ ID NO 12
<211> LENGTH: 16
```

```
<212> TYPE: PRT
<213> ORGANISM: Artificial Sequence
<220> FEATURE:
<223> OTHER INFORMATION: Synthetic peptide

<400> SEQUENCE: 12

Met Lys Thr Ile Ile Ala Leu Ser Tyr Ile Phe Cys Leu Val Phe Ala
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Gly Ser Pro Gly Gly Ala Ser Gly
1               5

<210> SEQ ID NO 14
<211> LENGTH: 1106
<212> TYPE: PRT
<213> ORGANISM: Homo sapiens

<400> SEQUENCE: 14

Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
                20                  25                  30

Leu Val Val Thr Pro Pro Gly Pro Glu Leu Val Leu Asn Val Ser Ser
                35                  40                  45

Thr Phe Val Leu Thr Cys Ser Gly Ser Ala Pro Val Val Trp Glu Arg
        50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
        130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
                195                 200                 205

Leu Gln Val Ser Ser Ile Asn Val Ser Val Asn Ala Val Gln Thr Val
        210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255
```

-continued

```
Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
                355                 360                 365

Thr Arg Asn Val Ser Glu Thr Arg Tyr Val Ser Glu Leu Thr Leu Val
        370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
                420                 425                 430

Thr Val Arg Cys Arg Gly Arg Gly Met Pro Gln Pro Asn Ile Ile Trp
                435                 440                 445

Ser Ala Cys Arg Asp Leu Lys Arg Cys Pro Arg Glu Leu Pro Pro Thr
        450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
                500                 505                 510

Ala Val Gly Gln Asp Thr Gln Glu Val Ile Val Val Pro His Ser Leu
                515                 520                 525

Pro Phe Lys Val Val Val Ile Ser Ala Ile Leu Ala Leu Val Val Leu
        530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
                580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
        610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
```

-continued

```
                675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
                740                 745                 750

Pro Met Leu Asp Met Lys Gly Asp Val Lys Tyr Ala Asp Ile Glu Ser
                755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
                820                 825                 830

Leu Ile Cys Glu Gly Lys Leu Val Lys Ile Cys Asp Phe Gly Leu Ala
                835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
                900                 905                 910

Phe Tyr Asn Ala Ile Lys Arg Gly Tyr Arg Met Ala Gln Pro Ala His
                915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
                980                 985                 990

Pro Gly Phe His Gly Leu Arg Ser  Pro Leu Asp Thr Ser  Ser Val Leu
                995                 1000                1005

Tyr Thr  Ala Val Gln Pro Asn  Glu Gly Asp Asn Asp  Tyr Ile Ile
    1010                1015                1020

Pro Leu  Pro Asp Pro Lys Pro  Glu Val Ala Asp Glu  Gly Pro Leu
    1025                1030                1035

Glu Gly  Ser Pro Ser Leu Ala  Ser Ser Thr Leu Asn  Glu Val Asn
    1040                1045                1050

Thr Ser  Ser Thr Ile Ser Cys  Asp Ser Pro Leu Glu  Pro Gln Asp
    1055                1060                1065

Glu Pro  Glu Pro Glu Pro Gln  Leu Glu Leu Gln Val  Glu Pro Glu
    1070                1075                1080

Pro Glu  Leu Glu Gln Leu Pro  Asp Ser Gly Cys Pro  Ala Pro Arg
    1085                1090                1095
```

```
Ala Glu  Ala Glu Asp Ser Phe  Leu
    1100                 1105

<210> SEQ ID NO 15
<211> LENGTH: 377
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
```

-continued

```
                355               360               365

Lys Ser Leu Ser Leu Ser Pro Gly Lys
    370               375

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tcatgcaggt tgacagcttc                                                    20

<210> SEQ ID NO 17
<211> LENGTH: 755
<212> TYPE: PRT
<213> ORGANISM: Artificial Sequence
<220> FEATURE:
<223> OTHER INFORMATION: Synthetic polypeptide

<400> SEQUENCE: 17

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
            115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
            195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
```

-continued

```
              275                   280                   285

Glu Cys Ala Ala Arg Gln Ala Thr Arg Glu Val Lys Glu Met Lys Lys
    290                   295                   300

Val Thr Ile Ser Val His Glu Lys Gly Phe Ile Glu Ile Lys Pro Thr
305                   310                   315                   320

Phe Ser Gln Leu Glu Ala Val Asn Leu His Glu Val Lys His Phe Val
                  325                   330                   335

Val Glu Val Arg Ala Tyr Pro Pro Arg Ile Ser Trp Leu Lys Asn
                  340                   345                   350

Asn Leu Thr Leu Ile Glu Asn Leu Thr Glu Ile Thr Thr Asp Val Glu
                  355                   360                   365

Lys Ile Gln Glu Ile Arg Tyr Arg Ser Lys Leu Lys Leu Ile Arg Ala
    370                   375                   380

Lys Glu Glu Asp Ser Gly His Tyr Thr Ile Val Ala Gln Asn Glu Asp
385                   390                   395                   400

Ala Val Lys Ser Tyr Thr Phe Glu Leu Leu Thr Gln Val Pro Ser Ser
                  405                   410                   415

Ile Leu Asp Leu Val Asp Asp His His Gly Ser Thr Gly Gly Gln Thr
                  420                   425                   430

Val Arg Cys Thr Ala Glu Gly Thr Pro Leu Pro Asp Ile Glu Trp Met
                  435                   440                   445

Ile Cys Lys Asp Ile Lys Lys Cys Asn Asn Glu Thr Ser Trp Thr Ile
    450                   455                   460

Leu Ala Asn Asn Val Ser Asn Ile Ile Thr Glu Ile His Ser Arg Asp
465                   470                   475                   480

Arg Ser Thr Val Glu Gly Arg Val Thr Phe Ala Lys Val Glu Glu Thr
                  485                   490                   495

Ile Ala Val Arg Cys Leu Ala Lys Asn Leu Leu Gly Ala Glu Asn Arg
                  500                   505                   510

Glu Leu Lys Leu Val Ala Pro Thr Leu Arg Ser Glu Gly Gly Gly Ser
                  515                   520                   525

Asp Lys Thr His Thr Cys Pro Pro Cys Pro Ala Pro Glu Leu Leu Gly
    530                   535                   540

Gly Pro Ser Val Phe Leu Phe Pro Pro Lys Pro Lys Asp Thr Leu Met
545                   550                   555                   560

Ile Ser Arg Thr Pro Glu Val Thr Cys Val Val Val Asp Val Ser His
                  565                   570                   575

Glu Asp Pro Glu Val Lys Phe Asn Trp Tyr Val Asp Gly Val Glu Val
                  580                   585                   590

His Asn Ala Lys Thr Lys Pro Arg Glu Glu Gln Tyr Asn Ser Thr Tyr
                  595                   600                   605

Arg Val Val Ser Val Leu Thr Val Leu His Gln Asp Trp Leu Asn Gly
    610                   615                   620

Lys Glu Tyr Lys Cys Lys Val Ser Asn Lys Ala Leu Pro Ala Pro Ile
625                   630                   635                   640

Glu Lys Thr Ile Ser Lys Ala Lys Gly Gln Pro Arg Glu Pro Gln Val
                  645                   650                   655

Tyr Thr Leu Pro Pro Ser Arg Glu Glu Met Thr Lys Asn Gln Val Ser
                  660                   665                   670

Leu Thr Cys Leu Val Lys Gly Phe Tyr Pro Ser Asp Ile Ala Val Glu
                  675                   680                   685

Trp Glu Ser Asn Gly Gln Pro Glu Asn Asn Tyr Lys Thr Thr Pro Pro
    690                   695                   700
```

-continued

```
Val Leu Asp Ser Asp Gly Ser Phe Phe Leu Tyr Ser Lys Leu Thr Val
705             710             715             720

Asp Lys Ser Arg Trp Gln Gln Gly Asn Val Phe Ser Cys Ser Val Met
                725             730             735

His Glu Ala Leu His Asn His Tyr Thr Gln Lys Ser Leu Ser Leu Ser
            740             745             750

Pro Gly Lys
        755
```